(12) United States Patent
Yi et al.

(10) Patent No.: US 7,449,694 B2
(45) Date of Patent: Nov. 11, 2008

(54) GAS SENSOR

(75) Inventors: Seung-Hwan Yi, Seoul (KR); Jeong-Ik Park, Seoul (KR); Ji-Hyun Kang, Seoul (KR)

(73) Assignee: Elt Inc. (KR)

( * ) Notice: Subject to any disclaimer, the term of this patent is extended or adjusted under 35 U.S.C. 154(b) by 0 days.

(21) Appl. No.: 10/596,390

(22) PCT Filed: Dec. 10, 2004

(86) PCT No.: PCT/KR2004/003243

§ 371 (c)(1),
(2), (4) Date: Jul. 10, 2007

(87) PCT Pub. No.: WO2005/057188

PCT Pub. Date: Jun. 23, 2005

(65) Prior Publication Data

US 2007/0279633 A1   Dec. 6, 2007

(30) Foreign Application Priority Data

Dec. 12, 2003 (KR) .................. 10-2003-0090539
Nov. 11, 2004 (KR) .................. 10-2004-0091776

(51) Int. Cl.
*G01J 5/08* (2006.01)
(52) U.S. Cl. ............................ 250/339.13
(58) Field of Classification Search .......... 250/339.1, 250/339.13
See application file for complete search history.

(56) References Cited

U.S. PATENT DOCUMENTS

| | | |
|---|---|---|
| 4,189,236 A | 2/1980 | Hogg et al. |
| 5,009,493 A | 4/1991 | Koch et al. |
| 5,116,120 A | 5/1992 | Picker |
| 5,170,064 A | 12/1992 | Howe |
| 5,341,214 A | 8/1994 | Wong |
| 5,444,249 A | 8/1995 | Wong |

(Continued)

FOREIGN PATENT DOCUMENTS

WO    WO 98/09152 A1    3/1998

(Continued)

OTHER PUBLICATIONS

Park, I. Y, et al. "An implementation of DIR type CO2 gas sample chamber and measuring hardware for capnograph system in consideration of the time response characteristics" Journal of Korean Sensor Society, vol. 5, No. 5, pp. 279-285, 2001.

(Continued)

*Primary Examiner*—David P. Porta
*Assistant Examiner*—Marcus H Taningco
(74) *Attorney, Agent, or Firm*—McKee, Voorhees & Sease, P.L.C.

(57) ABSTRACT

A unique optical cavity for NDIR gas sensor module and test results for the CO2 concentration from 100 ppm to 2,000 ppm are disclosed. The proposed sensor module shows the maximum peak voltage at 500 ms pulse duration, however, it has a maximum fractional voltage changes at 200 ms pulse duration with 18,000 times amplification gain. From 100 ppm to 2,000 ppm, the voltage difference of sensor module (V) is 200 mV at 200 ms pulse duration and 3 sec. turn-off time.

25 Claims, 29 Drawing Sheets

U.S. PATENT DOCUMENTS

| | | | |
|---|---|---|---|
| 5,488,227 A | 1/1996 | Sweet | |
| 5,767,967 A * | 6/1998 | Yufa | 356/336 |
| 5,973,326 A | 10/1999 | Parry et al. | |
| 6,067,840 A | 5/2000 | Chelvayohan et al. | |
| 6,194,735 B1 | 2/2001 | Martin | |

FOREIGN PATENT DOCUMENTS

| | | |
|---|---|---|
| WO | WO 99/41592 A1 | 8/1999 |

OTHER PUBLICATIONS

Noro, Makoto et al., "CO2/H20 Gas Sensor Using A Tunable Fabry-Perot Filter with Wide Wavelength Range" IEEE Conference on MEMS, pp. 319-322, 2003; 0-7803-7744-3.

Kaneyasu, K., et al. "A carbon dioxide gs sensor based on solid electrolyte for air quality control" 2000 Elsevier Sensors and Actuators B 66, pp. 56-58.

* cited by examiner

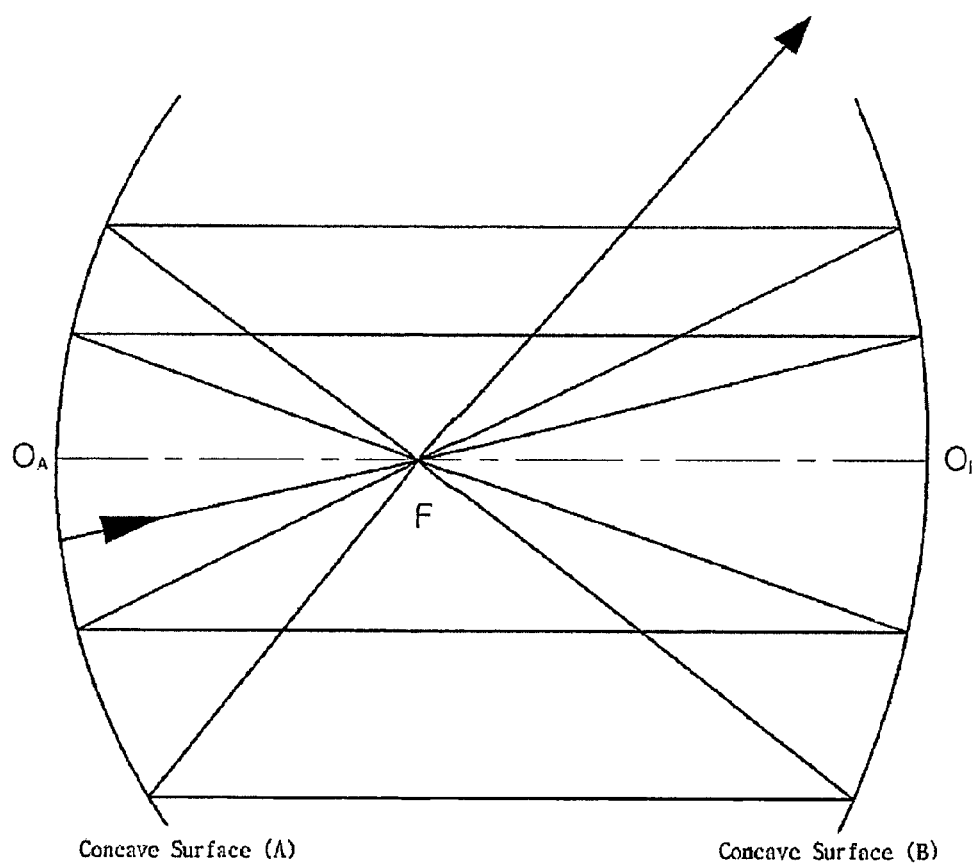

Optical Cavity (C)

Optical Cavity (C')

95　　　　　　135　125　　　　115 cf. 0.66*(0.97^2)=0.621 cf. 0.66*(0.97^5)=0.5667

GAS SENSOR

TECHNICAL FIELD

The present invention relates to an optical gas sensor and particularly, to a non-dispersive infrared gas sensor.

BACKGROUND TECHNOLOGY

The principle of operation of a conventional optical gas sensor is as below.

Generally, the light intensity is decreased or increased by diffraction, reflection, refraction and absorption of light on the optical path. As incident light passes through the optical path, a gas on the optical path absorbs the light and the initial light intensity decreases.

When the gas concentration (J) is isotropic and distributed uniformly on the optical path, and infrared light passes through the optical path (L), the final light intensity (I) can be explained by the Beer-Lambert's law, which is the function of the gas absorption coefficient (k), path length (L) and initial light intensity ($I_O$).

That is, $I = Io \cdot e^{-KJL(x)}$  Equation (1)

The Beer-Lambert's law is expressed as the above Equation (1). If the initial optical intensity ($I_O$) and the absorption coefficient of a gas to be measured are constant, the final light intensity (I) is expressed as a function of the gas concentration (J) on the optical path and the path length (L).

If there is no gas to be measured in the above Equation (1), i.e., if J=0, the final light intensity becomes equal to the initial light intensity.

That is, I=Io  Equation (2)

Hence, the difference of the light intensities between when there is no gas to be measured and when the gas concentration is J is obtained by Equation (3).

$\Delta I = Io \cdot (1 - e^{-KJL(x)})$  Equation (3)

However, since the conventional infrared sensor outputs a voltage in proportion to the light intensity, the output of the sensor according to the existence or non-existence of a gas is expressed as Equation (4).

$\Delta V = \alpha \cdot \Delta I = \alpha \cdot Io \cdot (1 - e^{-KJL(x)})$  Equation (4)

In order to produce an optical gas sensor having a broad range of measurement from low concentration to high concentration, first, an optical cavity (or a gas chamber) having long light path (L) should be provided; second, an infrared sensor of which the lowest limit of the detectable light intensity ($I_{th}$) is sufficiently low should be used; or third, an infrared sensor having a saturation light intensity ($I_{sat}$) which is relatively high and slightly smaller than the initial light intensity ($I_O$) radiated from an infrared source.

However, since the commercially available infrared detecting sensors (e.g., Thermopile IR sensor or Passive IR sensor) are not enough to satisfy all of the above conditions, an advantageous method of providing an optical cavity having long path is being required.

Various methods for extending the light path within a limited optical cavity have been suggested, one of which is U.S. Pat. No. 5,341,214 titled "NDIR GAS ANALYSIS USING SPECTRAL RATIONING TECHNIQUE" invented by Jacob Y. Wong. As illustrated in FIG. 1, the invention intends to provide an optical path tube structure that causes multiple reflections that result in the average path length being even greater than the physical length of the optical waveguide.

Also, it intends to increase the optical path by orienting the infrared emitted from the optical source to an arbitrary direction. However, an infrared gas sensor generally has a limited field of view for receiving incident light. Due to the limited field of view, the amount of light that substantially reaches the infrared sensor for measurement is very small. Hence, the efficiency of the gas chamber is low, and the practicality lacks.

There is another method, which uses the White's Cell principle, disclosed in U.S. Pat. No. 5,009,493 titled "MIRROR ARRANGEMENT FOR A BEAM PATH IN A MULTIPLE-REFLECTION MEASURING CELL." As illustrated in FIG. 2, a plurality of focuses lie on the reflection surfaces of mirrors, so that incident light can be reflected a predetermined number of time by the three arranged reflective mirrors, and the length of optical path can extend to analyze even a small amount of gases on the optical path.

However, since this kind of system uses a laser as source of light, it is not appropriate to measure gases like $CO_2$. Furthermore, it is difficult to be employed in a small gas detector due to the long distance between the reflection surfaces.

Still another method was proposed by Christopher R. Sweet in U.S. Pat. No. 5,488,227 titled "GAS ANALYZER", which constitutes a gas sensor by combination of a convex reflective mirror and a concave reflective mirror. In order to ensure an effectively long optical path, this method is characterized by installing a moving convex reflective mirror in a gas cell, as illustrated in FIG. 3. The gas analyzer according to this method comprises a structure (12) for ensuring a certain space within a gas sensor and preventing internal pollution, a cover (13), a cylindrical optical reflective mirror (15), a step motor (16) for rotating the mirror, an infrared sensor (24), a rotational disc (21) having a plurality of filters and a step motor (23) for rotating the disc.

However, since it is difficult to produce such a system and a step motor is needed for the rotation of the reflective mirror, it cannot be easily used in a small, portable and easy-to-use gas analyzer.

Still another method was disclosed in PCT/SE97/01366 (WO 98/09152) titled "GAS SENSOR" proposed by Martin. In order to provide a relatively long optical path in an optical cavity having a limited size, the method arranges three concave mirror surfaces as illustrated in FIG. 4. In other words, the gas sensor proposed by Martin comprises three elliptical concave surfaces, and it has an optical gas sensor cell structure, employing the White's cell concept of setting the focus of reflected light from each concave surface on or adjacent to the opposite reflection surface.

However, this gas sensor cell having three reflection surfaces is complex. Also, since the incident light, which is radiated from an optical source located on the surface of a main mirror (a mirror of one body) through an optical cavity, may have slight changes in its incident angle, it was difficult to determine the appropriate location of optical sensor.

The present invention relates to an optical gas sensor, more specifically to a non-dispersive infrared (NDIR) gas sensor.

There are two ways of measuring $CO_2$ concentration. One is NDIR system, and the other is solid electrolyte system as disclosed, for example, in "A carbon dioxide gas sensor based on solid electrolyte for air quality control" in *Sensors and Actuators B*. vol. 66, pp. 55-66, 2000 by K. Kaneyasu, et al.

Although the solid electrolyte sensor is less expensive than the NDIR sensor, the NDIR sensor is preferable in terms of long-term stability, high accuracy and low power consumption, etc. Also, the NDIR sensor has good selectivity and sensitivity since it employs the physical sensing principle that an objective gas absorbs infrared of a certain wavelength.

The optical characteristics of the NDIR sensor are as follows.

Generally, the light intensity is decreased or increased by diffraction, reflection, refraction and absorption of light on the optical path. As for an NDIR sensor, as the incident light passes through the optical path, a gas on the optical path absorbs it and the initial light intensity becomes decreased.

When the gas concentration (J) is isotropic and distributed uniformly on the optical path, and infrared light passes through the optical path (L), the final light intensity (I) can be explained by the Beer-Lambert's law, which is the function of the gas absorption coefficient (k), path length (L) and initial light intensity ($I_O$).

That is, $I = Io \cdot e^{-kJL(x)}$    Equation (5)

The Beer-Lambert's law is expressed as the above Equation (5). If the initial optical intensity ($I_O$) and the absorption coefficient (k) of a gas to be measured are constant, the final light intensity (I) is expressed as a function of the gas concentration (J) on the optical path and the path length (L).

If there is no gas to be measured in the above Equation (5), i.e., if J=0, the final light intensity becomes equal to the initial light intensity.

That is, I=Io    Equation (6)

Hence, the difference of the light intensities between when there is no gas to be measured and when the gas concentration is J is obtained by Equation (7).

$\Delta I = Io \cdot (1 - e^{kJL(x)})$    Equation (7)

However, since the conventional infrared sensor outputs a voltage in proportion to the light intensity, the output of the sensor according to the existence or non-existence of a gas is expressed as Equation (8).

$\Delta V = \alpha \cdot \Delta I = \alpha \cdot [Io \cdot (1 - e^{-kJL(x)})]$    Equation (8)

where, α is a proportional constant.

In order to produce an optical gas sensor having a broad range of measurement from low concentration to high concentration, first, an optical cavity (or a gas chamber) having long path (L) should be provided; second, an infrared sensor of which the lowest limit of the detectable light intensity ($I_{th}$) is sufficiently low should be used; and third, an infrared sensor having a saturation light intensity ($I_{sat}$) which is relatively high and slightly smaller than the initial light intensity ($I_O$) radiated from an infrared source.

However, the commercially available infrared detecting sensors (e.g., Thermopile IR sensor or Passive IR sensor) are not enough to satisfy all of the above conditions, an advantageous method of providing an optical cavity having long path is required.

There are four kinds of optical cavities that have been applied to existing NDIR gas sensor systems.

First, as disclosed in U.S. Pat. No. 5,444,249 of Jacob Y. Wong, which was issued on Aug. 22, 1995, there is a square type or a cylindrical tube type having one infrared (IR) source and one light detector.

Next, as disclosed in U.S. Pat. No. 6,067,840 invented by Mahesan Chelvayohan and issued on May 30, 2000 or as disclosed in the Article titled "An implementation of NDIR type $CO_2$ gas sample chamber and measuring hardware for capnograph system in consideration of time response characteristics" in *Journal of Korean Sensor Society*, vol. 5, no. 5, pp. 279-285, 2001 by I. Y. Park, et al., there is a type comprising one light detector and two IR optical sources for thermal aging compensation.

Third, what is disclosed in the Article titled "$CO_2/H_2O$ Gas Sensor Using Tunable Fabry-Perot Filter with Wide Wavelength Range" in the IEEE International Conference on MEMS, pp. 319-322, 2003 by Makoto Noro, et al. is a type using a cylindrical tube optical cavity and applying a Fabry-Perot filter for selecting target gas wavelength.

Fourth, what is disclosed in PCT/SE97/01366 (WO 98/09152) titled "Gas Sensor" dated Mar. 5, 1998 by Martin Hans, et al. is a type comprising three concave mirrors in order to increase the light path within a chamber of a small volume.

Particularly, the method proposed by Martin relates to an optical gas sensor cell structure comprising three concave reflection surfaces and applying the White's cell concept of setting the focus of reflected light on or adjacent to the opposite reflection surface. This method has an advantage of simply providing a relatively long optical path compared with other methods.

However, since the incident light, which is radiated from an optical source located on the surface of a main mirror (a mirror of one body) through an optical cavity, may have slight changes in its incident angle, it was difficult to determine the appropriate location of the optical sensor.

DETAILED DESCRIPTION OF THE INVENTION

The present invention has been conceived in order to resolve the aforesaid problems. The object of the present invention is to maximize the length of the optical path and to provide an optical gas sensor having a broad measurement ranges with an optical cavity (or a gas chamber) structure that can be easily designed.

Also, the present invention provides a new optical cavity structure for a new optical gas sensor cell, and presents a new gas sensor based on the $CO_2$ concentration measurement experiment result of a sensor employing such an optical cavity.

For the aforesaid object, the optical gas sensor according to one aspect of the present invention comprises a gas chamber for housing a sample gas; a gas opening for injecting a sample gas into the gas chamber or for exhausting the sample gas from the gas chamber; an optical source for projecting infrared toward the sample gas; and an infrared sensor for sensing the intensity of the infrared which has passed through the sample gas, wherein the wall of the gas chamber is composed of two opposing concave mirrors having different focusing distances but a common focus.

For the aforesaid object, the optical gas sensor according to another aspect of the present invention comprises a gas chamber for housing a sample gas; a gas opening for injecting a sample gas into the gas chamber or for exhausting the sample gas from the gas chamber; an optical source for projecting infrared toward the sample gas; and an infrared sensor for sensing the intensity of the infrared which has passed through the sample gas, wherein the wall of the gas chamber is composed of two opposing concave mirrors having different focusing distances but a common focus, and the concave mirrors have curvatures such that the incident light which is parallel to the axis of the concave mirror reflects on the surface of the concave mirror and passes through the focus of the concave mirror, and that the incident light, which has passed through the focus of the concave mirror reflects on the surface of the concave mirror and propagates parallel to the axis of the concave mirror.

The gas openings comprise a gas vent established at a certain wall of the gas chamber and a plurality of gas diffusion holes disposed on the lower or upper support plate of the gas chamber.

The plurality of gas diffusion holes is covered by a gas filter.

The plurality of gas diffusion holes is preferably disposed on the axis of the incident light from the infrared sensor.

The gas vent is advantageously curved downward or it can be equipped with a detachable cap.

The surface of the concave mirror is produced with gold plating or gold deposition.

The gas chamber contains a parabolic reflecting mirror integrally formed with the support plate of the gas chamber adjacent to the infrared optical source formed at the support plate.

The gas chamber has a light outlet for projecting at least a part of the infrared light from the infrared optical source on the support plate.

The infrared optical source can be disposed on the focus of the parabolic mirror.

The support plate of the gas chamber may comprise a height compensation structure for the inclination of the support plate due to the height of the infrared optical source.

Figure 1:
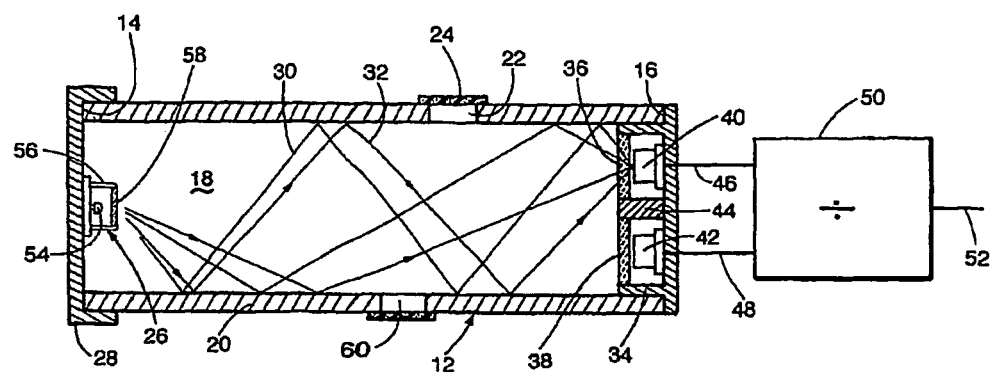
FIGS. 1-4 illustrates an optical gas sensor of the prior art.
Figure 2:
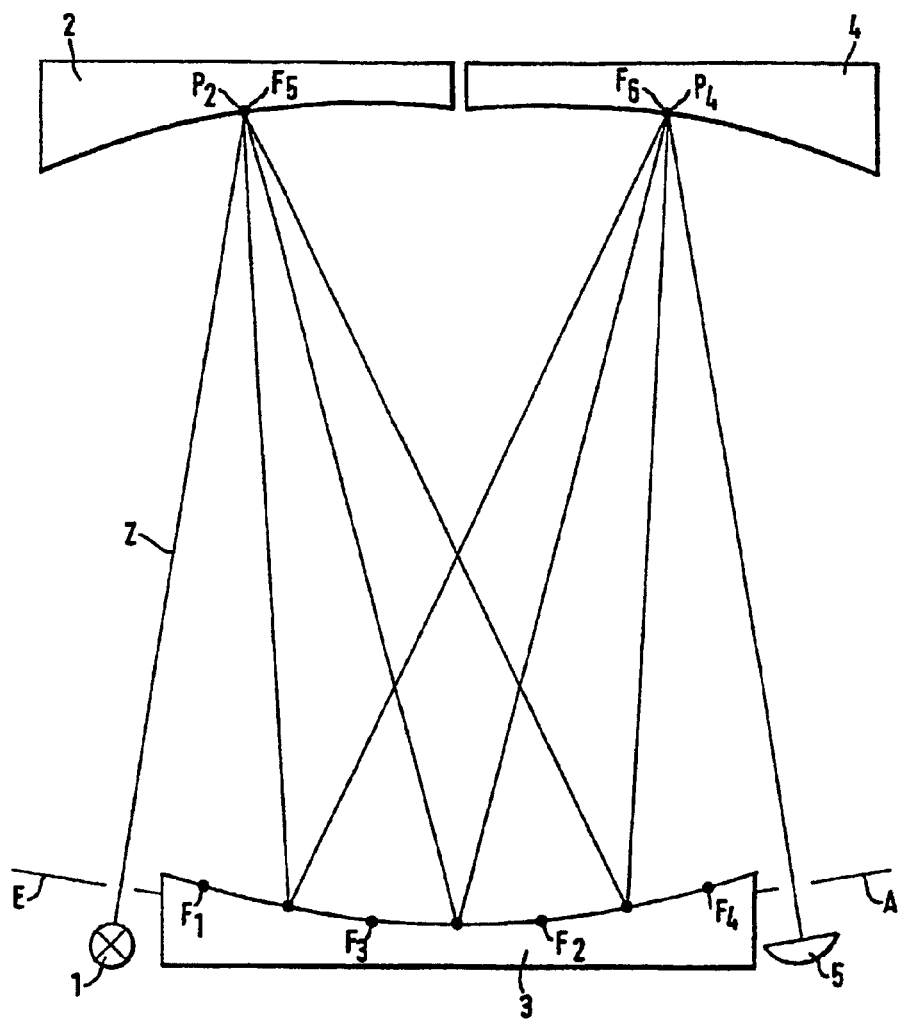
Figure 3:
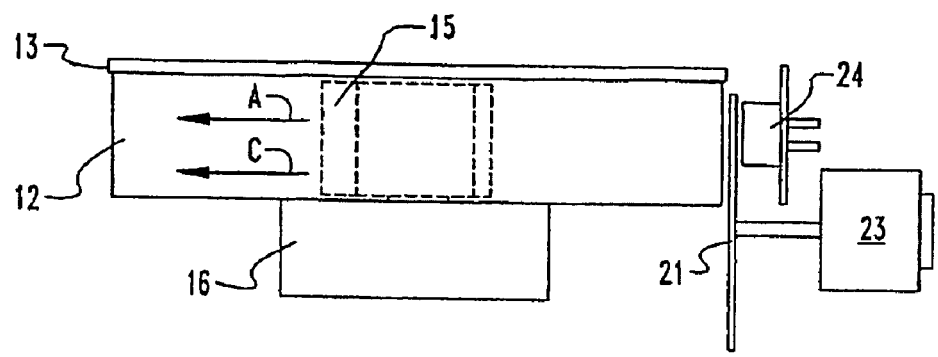
Figure 4:
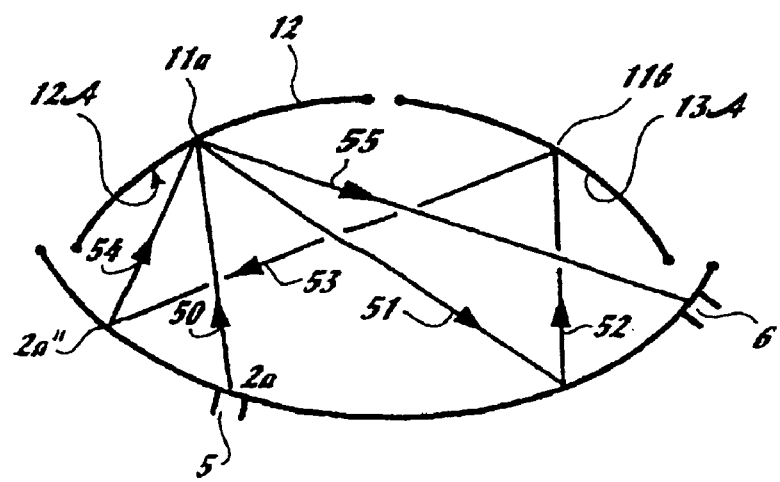

TERMS OF THE ESSENTIAL CONSTITUENTS
IN THE DRAWINGS 10, 15: gas chamber lower support plates
20: a first mirror
25: a first parabolic reflective mirror
30: a second mirror
35: a second parabolic reflective mirror
40, 45: gas vents
50, 55: parabolic mirrors
60, 65: infrared sensors
70, 75: gas chamber upper plates
80, 85: optical outlets
90, 95: infrared lamps
100: a cap
110, 115: height compensation structures
120, 125: gas diffusion holes
130, 135: gas filters Embodiments of the present invention will now be described with reference to the accompanying drawings.

Figure 5:
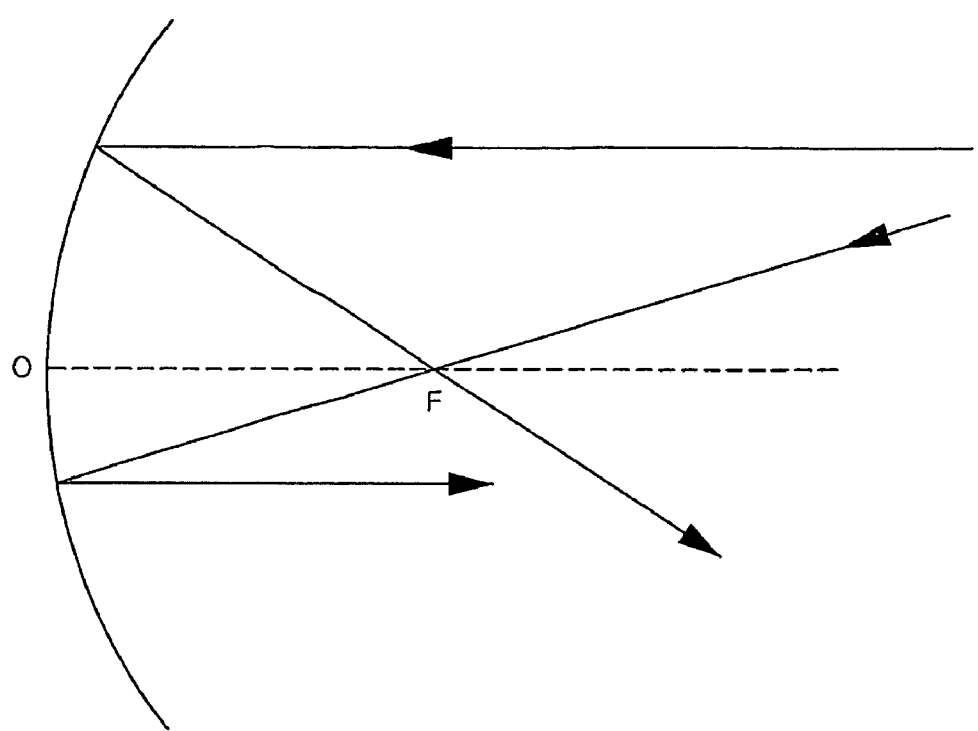
FIG. 5 shows an optical characteristic of a parabola-shaped mirror.

FIG. 5 shows an optical characteristic of a parabolic reflective mirror.

As illustrated in FIG. 5, in case of a parabolic reflective mirror, the reflected light of an incident light which has entered parallel to the optical axis always passes through the focus of the reflective mirror, and the reflected light of and incident light which has passed the focus of the mirror always propagates parallel to the optical axis.

The present invention uses these optical characteristics of a parabolic reflective mirror.

FIG. 6 shows an optical characteristic of an optical cavity system having two parabolic reflective mirrors having a common focus.

The optical cavity system illustrated in FIG. 6 is arranged such that two parabolic reflective mirrors are opposed to each other to have a common focus, and two focal lengths ($O_A$-F, $O_B$-F) of the two parabolic reflective mirrors are not identical.

According to the position of light source, the optical cavity system is classified into a divergence system (FIG. 6a), in which an incident light is diverged in the optical cavity, and a convergence system (FIG. 6b), in which an incident light is converged in the optical cavity.

Figure 6B:
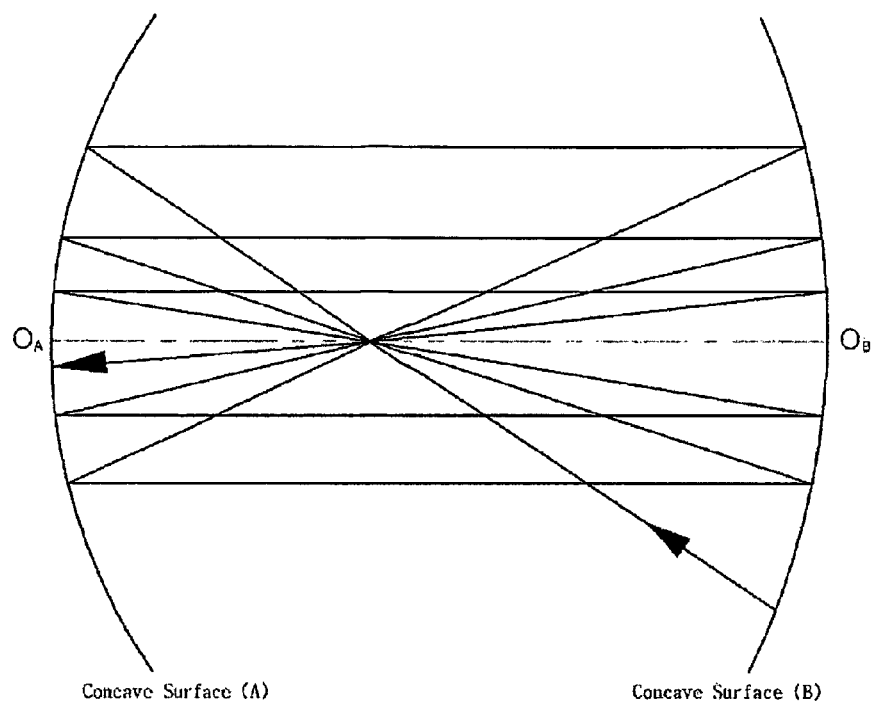
FIG. 6 shows an optical feature of an optical cavity system having two parabolic mirrors having a common focus.

As illustrated in FIG. 6b, which satisfies condition $O_A$-F<$O_B$-F, if light enters from a concave surface (B) toward a focus F on the optical axis, the light passes through the focus and then it reflects from a concave surface (A) to be parallel to the optical axis. The reflected light repeats the process of being reflected again from the concave surface (B) until it converges into the optical axis and finally reaches the concave surface (A) or (B). Also, the light, which has converged into the optical axis, is reflected and recurred to the direction where it entered.

Divergence system also experiences the same process as the above convergence system, then the irradiated light, which has diverged from the optical axis, is located at the concave surface (A) or (B).

FIG. 7 illustrates an optical path according to the different focal distance of two parabolic reflective mirrors having a common focus.

Figure 7A:
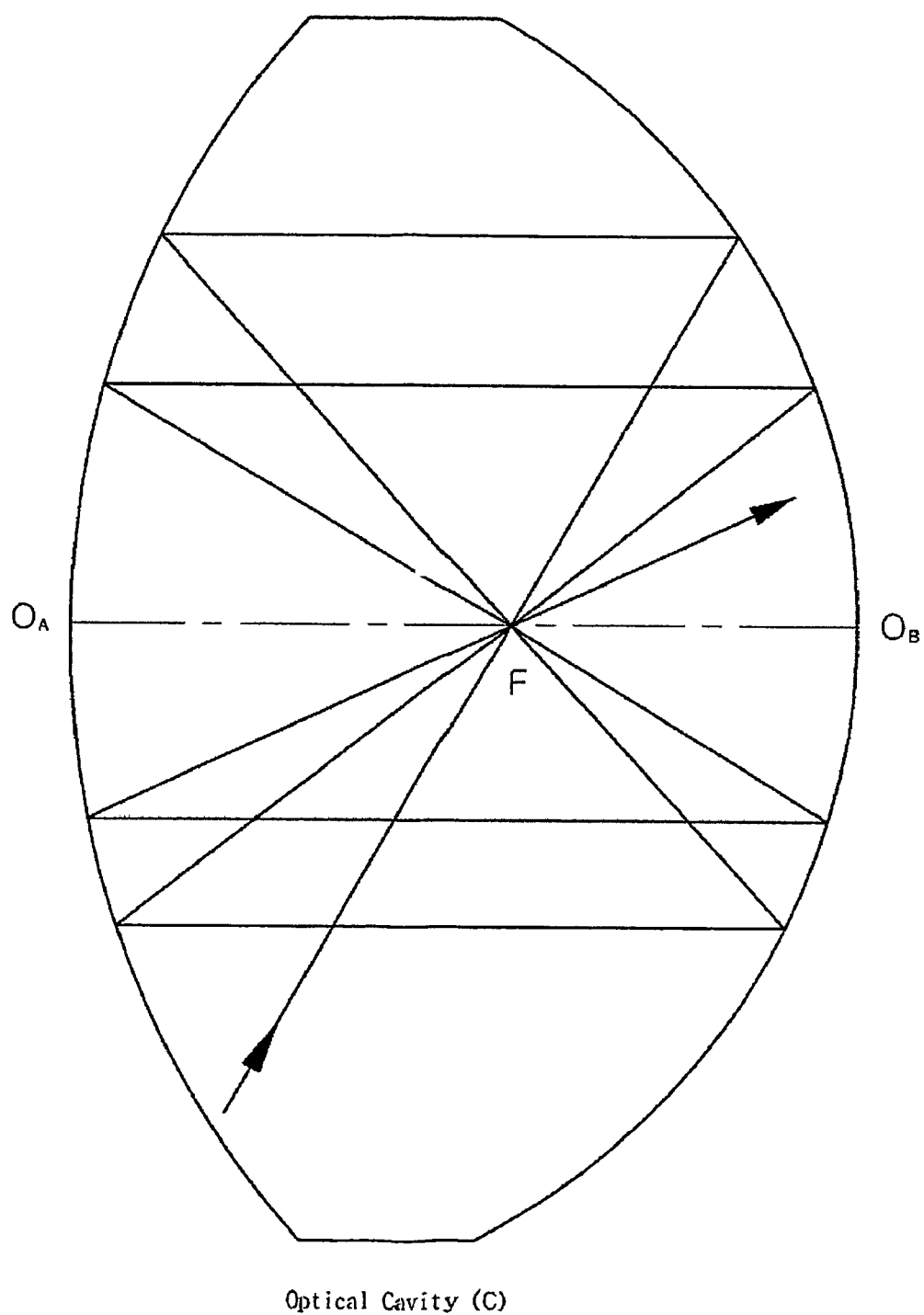
FIG. 7 illustrates an optical path according to the differences in the focusing distances of two parabolic mirrors having a common focus.
Figure 7B:
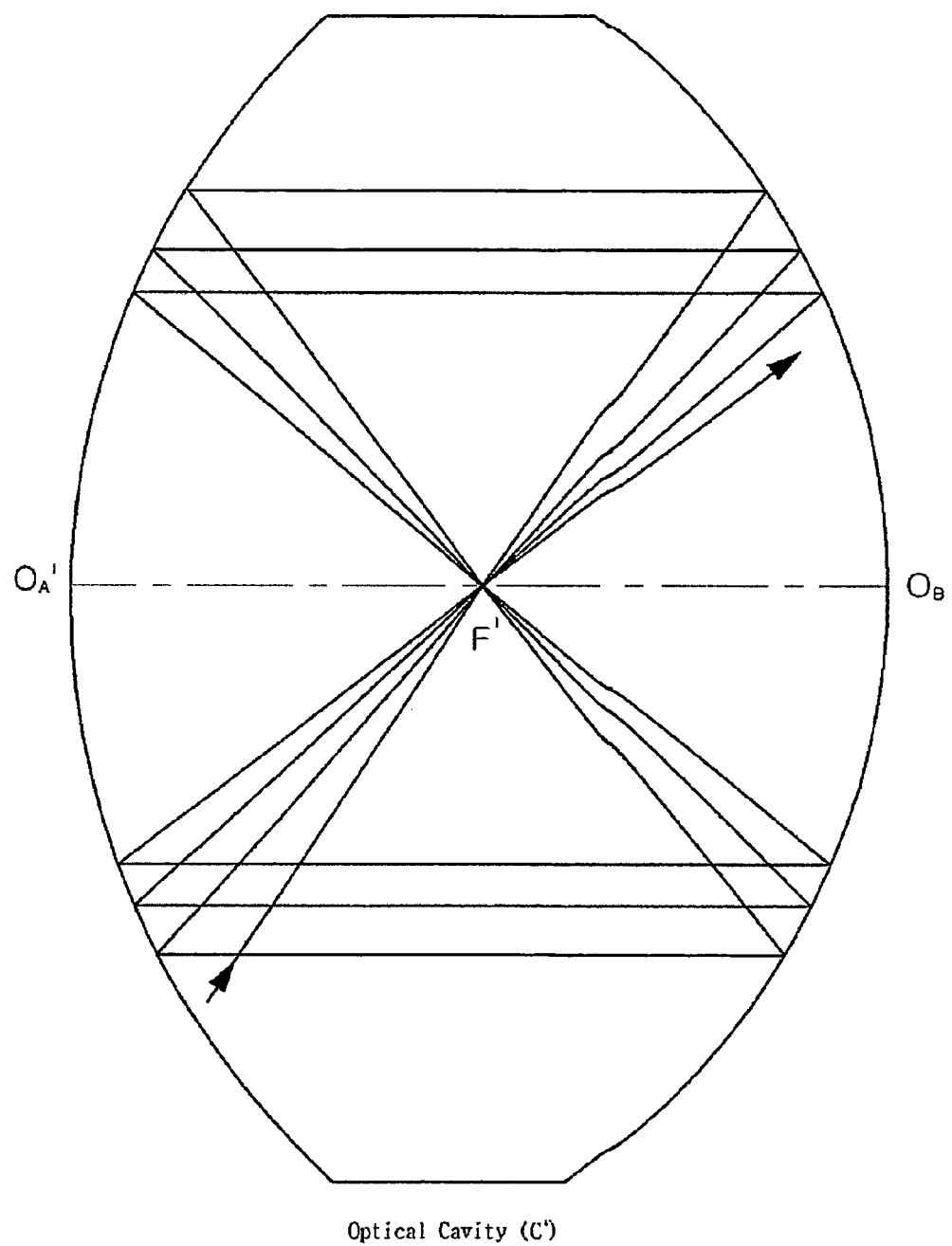

As illustrated in FIG. 7(b), an optical cavity system wherein $O_A$F-$O_B$F>$O_A$'F-$O_B$'F has a feature that the optical path of optical cavity (C') is longer than that of optical path (C) since the number of optical reflection in the optical cavity (C') is more than that in the optical cavity (C) illustrated in FIG. 7(a).

As stated above, in the optical cavity system, wherein two parabolic reflective mirrors are opposed to each other so that they have a common focus and the two focal distances ($O_A$-F, $O_B$-F) of two parabolic reflective mirrors are not identical, the length of the optical path can be controlled by changing the focal distance, and also the optical path can be controlled by changing the angle of the optical axis and the incident angle.

Also, since the two parabolic reflective mirrors have a common focus and different focal distance and the incident light converges into the optical axis, the location establishment of an infrared sensor becomes easy.

The optical gas sensor according to the present invention causes light reflections on the optical path between an optical source and an infrared sensor as many as possible by using the aforesaid optical characteristic of the optical cavity system, thereby lengthening the optical path in an optical cavity of a given size. Hereinafter, embodiments of the optical gas sensor according to the present invention will be described.

Figure 8:
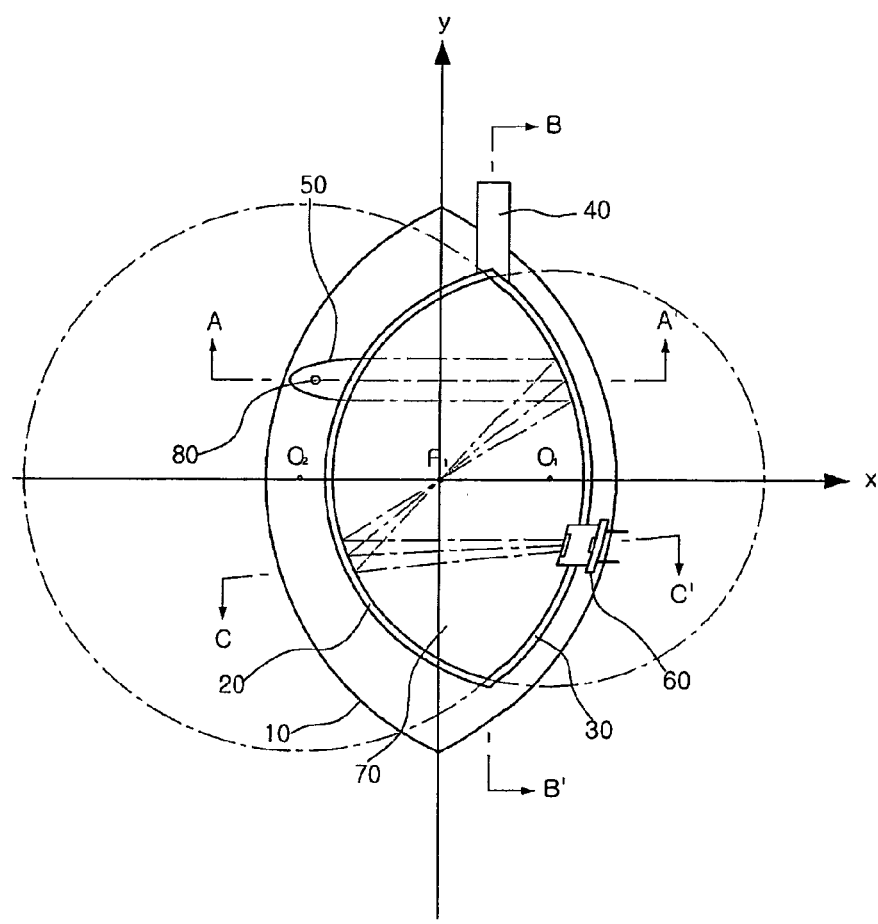
FIG. 8 is a top plane view of an optical gas sensor according to one embodiment of the present invention.

FIG. 8 is a top plane view of an optical gas sensor according to one embodiment of the present invention.

The optical gas sensor according to one embodiment of the present invention comprises a gas chamber, a gas vent (40), a parabolic mirror (50), an infrared sensor (60), an optical outlet (80), an infrared lamp (90), a height compensation structure (110), gas diffusion holes (120) and a gas filter (130), wherein said gas chamber comprises a gas chamber lower support plate (10), a first mirror (20), a second mirror (30) and a gas chamber upper plate (70).

Upon reviewing the top plane view of the optical gas sensor illustrated in FIG. 8, the optical gas sensor comprises a gas chamber of a closed optical cavity that consists of a lower support plate (10), a gas chamber upper plate (70) and a chamber wall.

The gas chamber wall consists of a first mirror (20) and a second mirror (30), wherein said first mirror (20) and said second mirror (30) have a common focus ($F_1$), and they are configured as partial-circular-arcs having different curvature radii.

The reason for using two circular-arc-shaped mirrors is that in case of a circle, a focus is formed at the ½ point of the diameter, which works like a parabola. If light is irradiated parallel to the optical axis, the path of reflected light is determined as the focus or adjacency of the focus. Thus, a certain portion of the circular-arc-shaped mirror shows a very similar or identical optical characteristic to that of a parabolic mirror.

An opening for irradiating infrared radiated from an infrared lamp (not shown) is formed in the first mirror (20), and a parabolic mirror (50) is formed on the gas chamber lower support plate (10). The parabolic mirror (50) ensures straightforward radiation of light from the infrared lamp.

In addition, an optical outlet (80) for irradiating only partial infrared that is radiated from the infrared lamp is formed on the gas chamber lower support plate (10).

The infrared sensor (60) for detecting light irradiated from the infrared lamp is disposed on the second mirror (30). A gas vent (40) for injecting a reference gas to identify the optical characteristic of the optical gas sensor and to perform initial correction is disposed at the position where the first mirror (20) meets the second mirror (30).

Upon reviewing the optical path of the optical gas sensor having aforesaid constitution, as illustrated in FIG. 8, infrared light, which has been introduced parallel to the optical axis through the parabolic mirror (50), proceeds toward the second mirror (30). Subsequently, the infrared light, which has been reflected by the second mirror (30), passes through the common focus ($F_1$) or adjacent to the common focus ($F_1$) of the first mirror (20) and the second mirror (30) and is reflected by the first mirror (20). Finally, the converged infrared light reaches the infrared sensor (60) disposed on the second mirror (30).

Meanwhile, in order to minimize loss and scattered reflection of light when light is reflected from the wall of a gas chamber, the gas chamber can be made of a metal. In this event, scattered reflection can be reduced by mirror like finishing through surface polishing inside of the metal.

At the time of producing a gas chamber made of a non-metallic material, loss of light can be minimized by coating a material layer having high reflectivity such as gold, nickel, silver and copper or twofold layer of gold/chrome on the chamber wall.

Following Table-1 shows reflectivity of various metals according to optical wavelength. It shows that gold and silver have at least 98% reflectivity at the optical wavelength of 800 nm or more, and aluminum and copper have at least about 94% reflectivity at the optical wavelength of 1 μm or more. However, generally, silver, aluminum and copper, etc. are oxidized automatically and changed of its color if humidity is high at an ordinary temperature. Thus, in order to prevent aging and ensure long time reliable reflective surface, it is preferable to process the chamber surface with gold.

TABLE 1

Reflectivity of various metals according to optical wavelength

| Optical wavelength | Optical reflectivity according to wavelength (%) | | | |
|---|---|---|---|---|
| | Au | Ag | Al | Cu |
| 200 nm | 23 | 23 | 91 | 40 |
| 400 nm | 39 | 96 | 92 | 47 |
| 600 nm | 92 | 98 | 91 | 93 |
| 800 nm | 98 | 99 | 87 | 98 |
| 1 μm | 99 | 99 | 94 | 98 |
| 2 μm | 99 | 99 | 98 | 98 |
| 4 μm | 99 | 99 | 98 | 99 |
| 5 μm | 99 | 99 | 98 | 99 |

Hence, for efficient reflection of infrared light, preferably, the reflection surfaces of the first mirror (20) and the second mirror (30) are coated or deposited with gold or gold/chrome.

Figure 9:
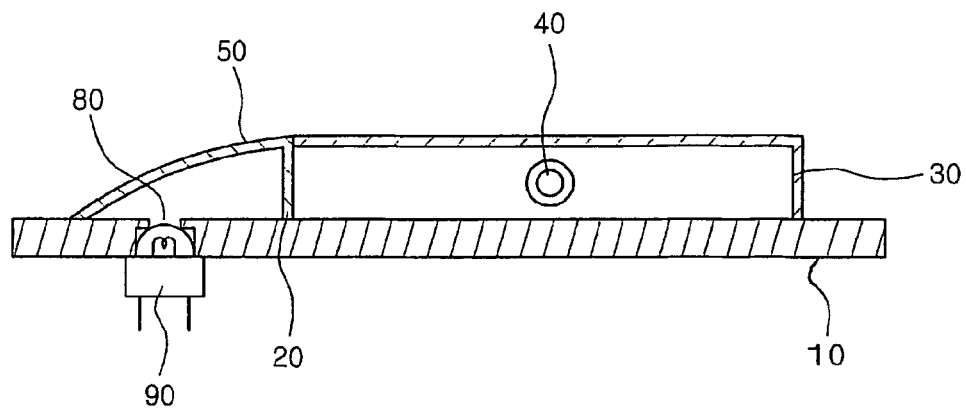
FIG. 9 is a sectional view of A-A' of the optical gas sensor illustrated in FIG. 8.

FIG. 9 is a cut-away sectional view of A-A' of the optical gas sensor illustrated in FIG. 8. Upon reviewing FIG. 9, an optical vent (80) for introducing infrared light radiated from the infrared lamp (90) to the optical cavity is formed at the gas chamber lower support plate (10), and a parabolic mirror (50) for ensuring the straightness of incident light radiated from the infrared lamp is formed in a manner as being connected to the first mirror (20) and the gas chamber lower support plate (10).

The infrared lamp (90) is established at the lower part of the gas chamber lower support plate (10), and disposed on the focus of the parabolic mirror (50).

Figure 10:
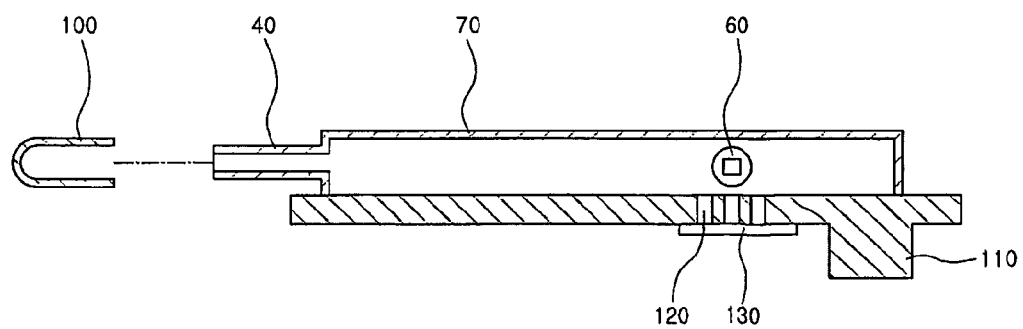
FIG. 10 is a sectional view of B-B' of the optical gas sensor illustrated in FIG. 8.

FIG. 10 is a cut-away sectional view of B-B' of the optical gas sensor illustrated in FIG. 8. Upon reviewing FIG. 10, a cap (100) coupled to the gas vent (40) for preventing the gas chamber from being polluted by dust, for example, is shown. The cap (100) can be separated from the gas vent (40).

A plurality of diffusion holes (120) for rapidly diffusing gas is formed on the gas chamber lower support plate (10). The gas diffusion holes (120) are covered with a gas filter (130) for selectively permeating only gas and avoiding diffusion of dust and humidity. Meanwhile, a height compensation structure (110) for compensating the height difference due to the infrared lamp (90) is formed under the gas chamber lower support plate (10).

Figure 11:
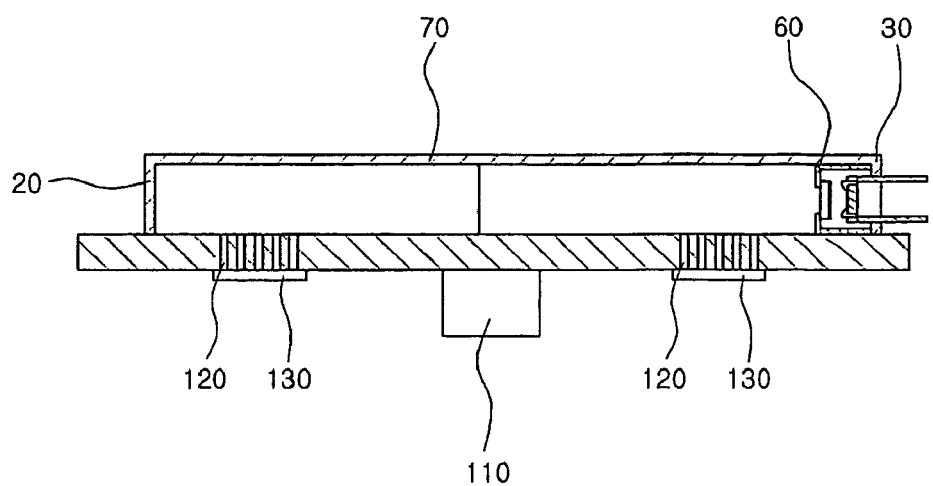
FIG. 11 is a sectional view of C-C' of the optical gas sensor illustrated in FIG. 8.

FIG. 11 is a cut-away sectional view of C-C' of the optical gas sensor illustrated in FIG. 8. Upon reviewing FIG. 11, it can be understood that the plurality of diffusion holes (120) formed on the gas chamber lower support plate (10) are preferably formed on the same optical axis as the infrared sensor (60).

Figure 12:
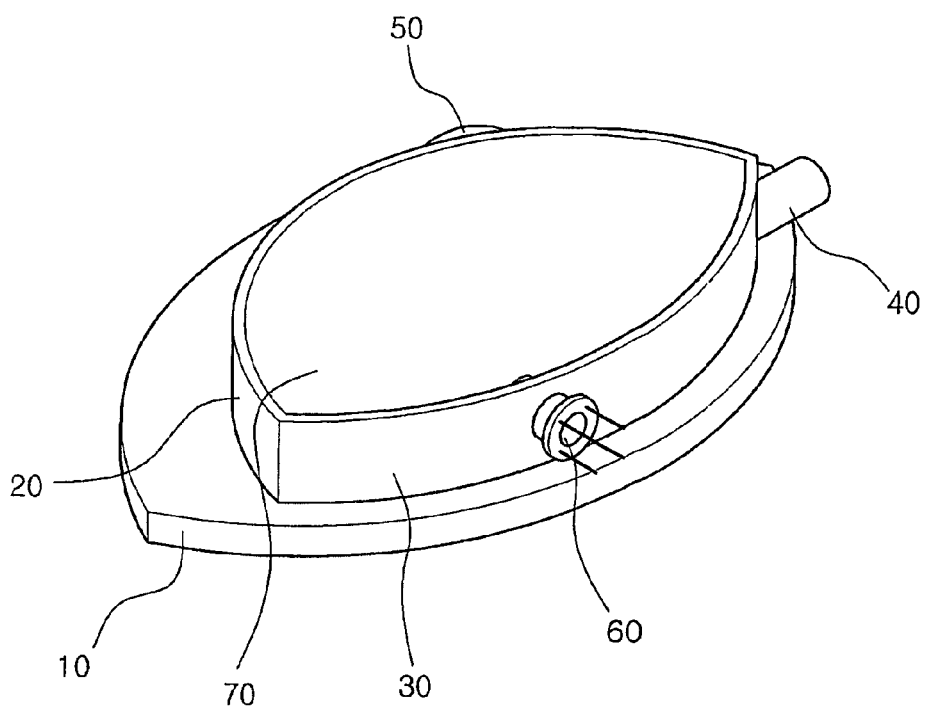
FIG. 12 is a perspective view of an optical gas sensor according to one embodiment of the present invention.

FIG. 12 is a perspective view of the optical gas sensor reviewed in the above FIGS. 8-11 according to one embodiment of the present invention.

Figure 13:
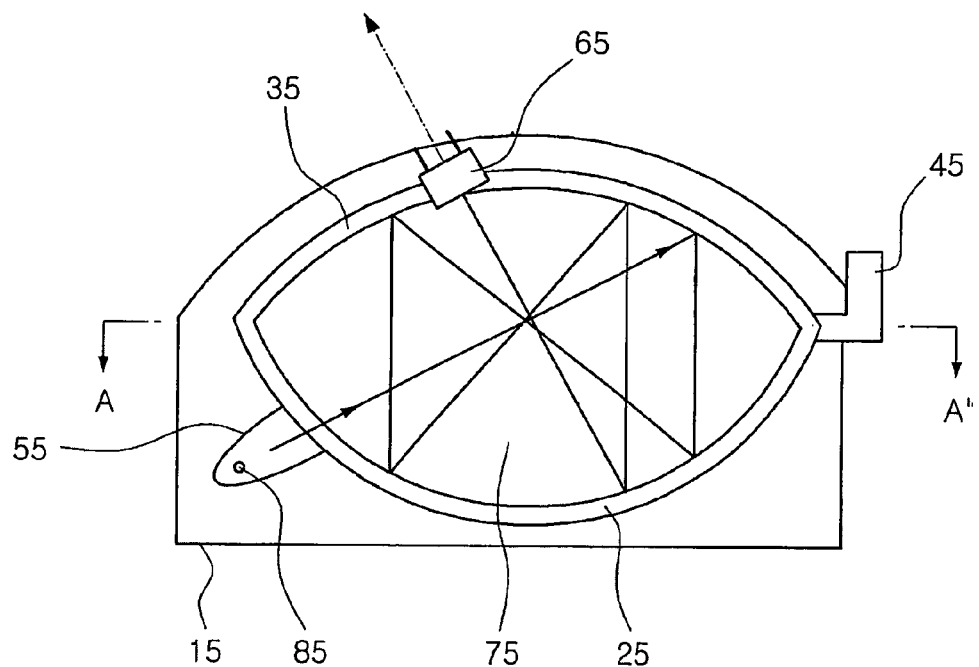
FIG. 13 is a top plane view of an optical gas sensor according to another embodiment of the present invention.
Figure 14:
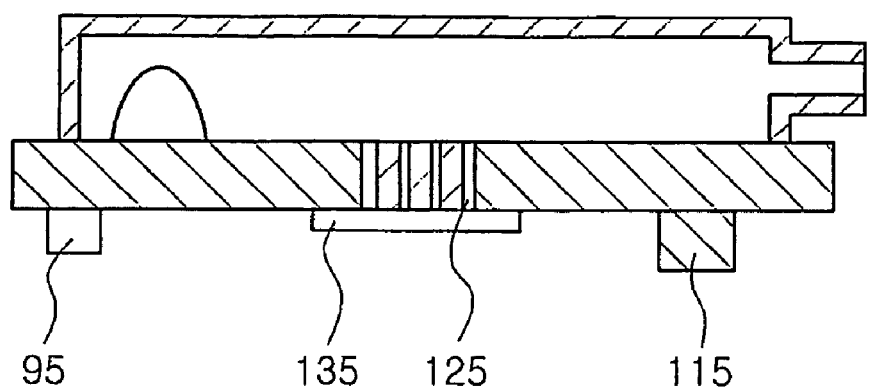
FIG. 14 is a sectional view of A-A' of the optical gas sensor illustrated in FIG. 13.

FIG. 13 is a top plane view of an optical gas sensor according to another embodiment of the present invention. FIG. 14 is a sectional view of A-A' of the optical gas sensor illustrated in FIG. 13.

The structure of the optical gas sensor illustrated in FIG. 13 is nearly the same as that of the optical gas sensor of the above FIGS. 8-12 except that two mirrors forming a gas chamber wall are configured as parabolas instead of circular arcs.

In other words, the gas chamber wall of the optical gas sensor illustrated in FIG. 13 uses two opposing parabolic reflective mirrors having a common focus but different focal distance. Also, a gas vent (45) is curved in the direction of gravity to prevent internal pollution of the gas chamber.

Upon reviewing the operation principle of the optical gas sensor illustrated in FIGS. 13 and 14, infrared light radiated through an infrared lamp (95) passes via an optical outlet (85) and a parabolic mirror (55), and is entered into the gas chamber.

The incident light is entered toward the common focus of a first parabolic reflective mirror (25) and a second parabolic reflective mirror (35), reflected by the first and second parabolic reflective mirrors (25, 35) and converged. The light intensity is measured at an infrared sensor (65).

Although the present invention has been described with reference to particular embodiments, the description is only an example of the present invention. Various adaptations and combinations of features of the embodiments disclosed are within the scope of the invention as defined by the accompanied claims.

Further object of the present invention is to produce an optical cavity for non-dispersive infrared gas sensor, comprising two concave mirrors which are opposed to each other, of which the section is a circular arc, of which the central point is located on the same axis, and which are optically closed except for an inlet for establishing an optical source, an outlet for establishing a light detector and gas inlet/outlets.

Also, further object of the present invention can be achieved by a non-dispersive infrared gas sensor comprising an optical source for irradiating infrared; a light detector for ultimately detecting light from the optical source; an optical cavity which is formed by two opposing concave mirrors of which the cross-section is a circular arc, of which the central point is located on the same axis, and which are optically closed except for the inlet for establishing an optical source and the outlet for establishing a light detector and gas in/outlets; an optical modulating part having a pulse modulation time of 200-600 ms and turn-off time of 2, 2.5 and 3 sec. for controlling the light irradiated from the optical source; and an amplification part for amplifying an electrical signal from the light detector.

Hereinafter, further aspects of the present invention will be further explained with reference to the drawings illustrated in the embodiments of the present invention. Basically, the optical cavity of the present invention is produced by circular arcs.

Basically, the optical cavity of the present invention is produced by circular arcs. The central point of the two circular arcs exists on the same axis.

Also, the embodiments of the present invention design the central point of each circular arc to be identical with the middle point of the straight line going from one circular arc to the other circular arc (the two centers of two circular arcs exist on the same straight line). The reason thereof is for irradiated light under a certain condition to be able to pass via a certain point on the same straight line (if the feature of a circular arc is applied identically with a parabola, the circular arcs are designed to pass via an identical focus). The reason for endowing this condition is, for example, to ensure the characteristic of a parabola also for a circular arc so that light entered into the mirror in parallel to the axis is converged into a focus. In other words, if the invention is designed as the above-proposed structure, the light irradiated horizontally to the axis is reflected on each mirror, heads for opposing surfaces and focuses at a certain point. As shown in the following result of trial experiments, it is because of the feature of parallel light being focused on the optical path.

Meanwhile, the above embodiments of the present invention are designed that two circular arcs have different radii, the central point of a circular arc having a longer radius exists outside of the circular arc having a shorter radius, and the central point of a circular arc having a shorter radius exists inside of the circular arc having a longer radius. In this case, it was experimentally confirmed that the optical path from an optical source to a light detector makes a proper number of circulations.

Under the condition in which all the above conditions are satisfied, in order to derive an optical cavity design for obtaining a light convergence effect and an optical cavity design for effectively increasing the optical path, optical simulations have been conducted as follows.

In the simulations, an infrared optical source having 4.2 μm wavelength and input power of 0.66 watt, which is the consumption power under steady state operation, have been set. Also, the inside of the optical cavity has been coated with gold (Au) to simulate a mirror having approximately 97% reflectivity. This is because a gold thin film having a certain thickness has at least 97% reflectivity in the infrared range, particularly at the wavelength of 1 μm or more. Also, incident light is parallel light that enters into the inlet hole vertically. Meanwhile, the shape, size and configuration of an active area, etc. of the light detector have been set to be identical with those of a commercially applicable infrared sensor. Also, a program of TracePro® of Lambda Research Corporation has been used as an analysis tool for the simulations.

Figure 15A:
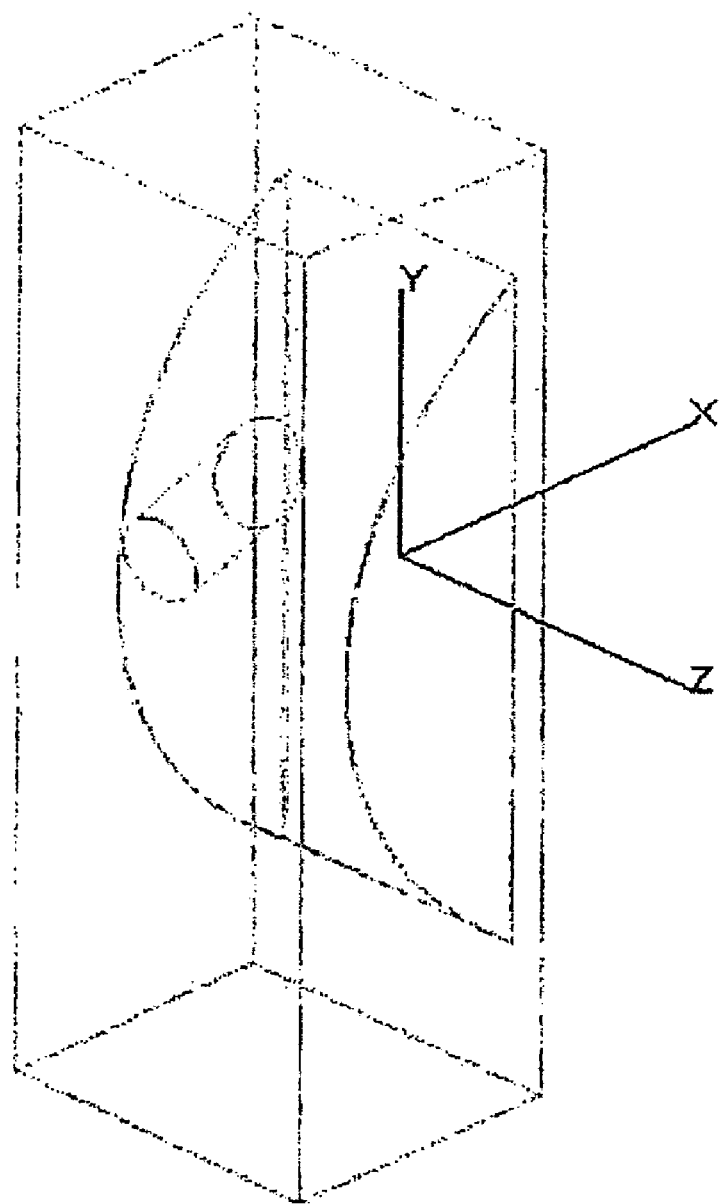
FIG. 15a shows a left half of an optical cavity according to one embodiment of the present invention.
Figure 15B:
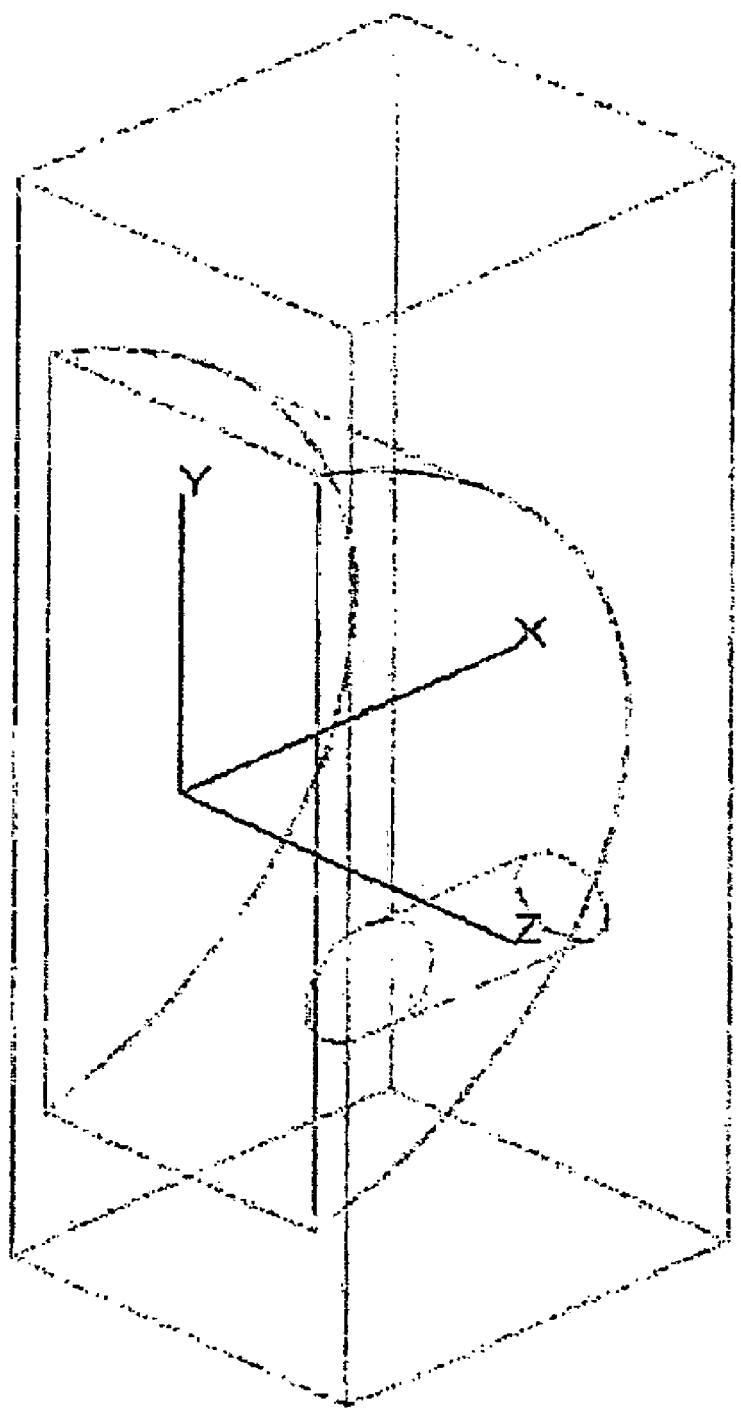
FIG. 15b shows a right half of an optical cavity according to one embodiment of the present invention.
Figure 15C:
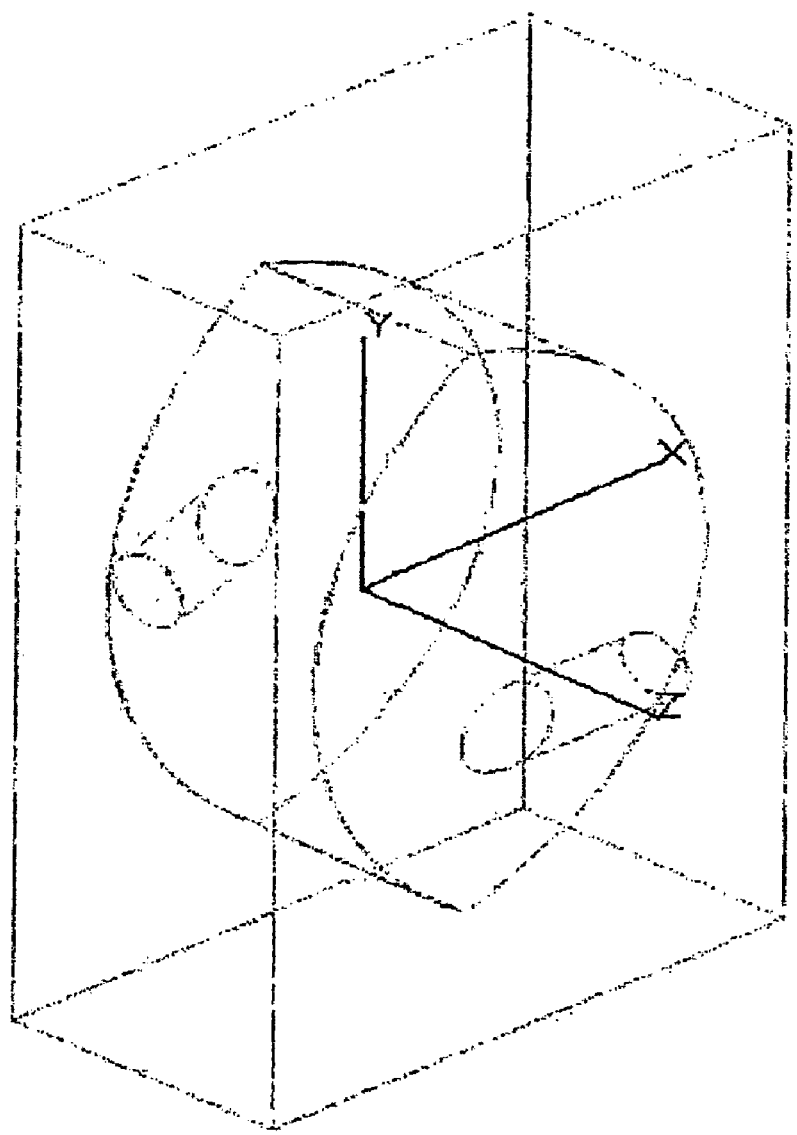
FIG. 15c shows the optical cavity assembled together according to the above embodiment.

In a first simulation, an optical structure, which is illustrated in FIGS. 15a, 15b and 15c, has been applied. The optical cavity of FIG. 15c is a combination of the left half of FIG. 15a and the right half of FIG. 15b. This is one example of a design for lowering manufacturing cost for an initial test and facilitating deposition of a gold thin film of a mirror. This combination is only an example, so another optical cavity having different combination still be possible. In other words, it is possible to produce an integral optical cavity through a mold, and deposit gold or coat with gold on the surface.

In the first simulation, the optical cavity has been designed that the optical path can be checked and that the focusing effect of light can be achieved to increase the amount of light detected by the optical detector while maintaining the size of the optical cavity to be small. In other words, as shown in Equation (8), in order to measure a very slight amount of gas, firstly, the length of optical path should be increased in the optical cavity, secondly, an infrared sensor having small lowest light intensity ($I_{th}$) capable of detecting infrared is used, or thirdly, an infrared sensor having saturation light intensity ($I_{sat}$) that is relatively great but slightly smaller than the initial light intensity ($I_o$) radiated from an infrared optical source can be used. In addition to the methods, there is a method of increasing the intensity of light reaching an infrared sensor through the focusing of light. Hereinafter, the present invention will be explained with reference to the drawings.

Figure 16:
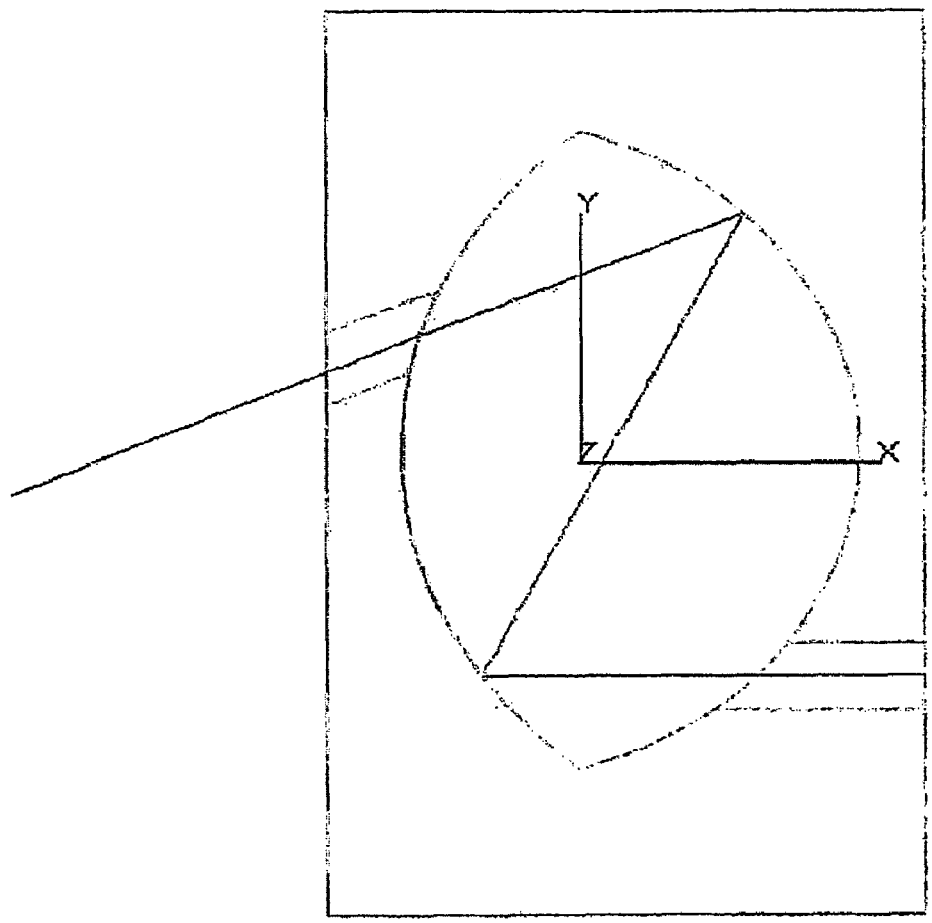
FIG. 16 is an optical path generated from the optical cavity structure according to the above embodiment.

FIG. 16 is an optical path generated from the optical cavity structure illustrated in FIG. 15c.

FIG. 16 illustrates the optical path of incident light, which provides useful information enabling to calculate the optical length in the optical cavity.

Figure 17:
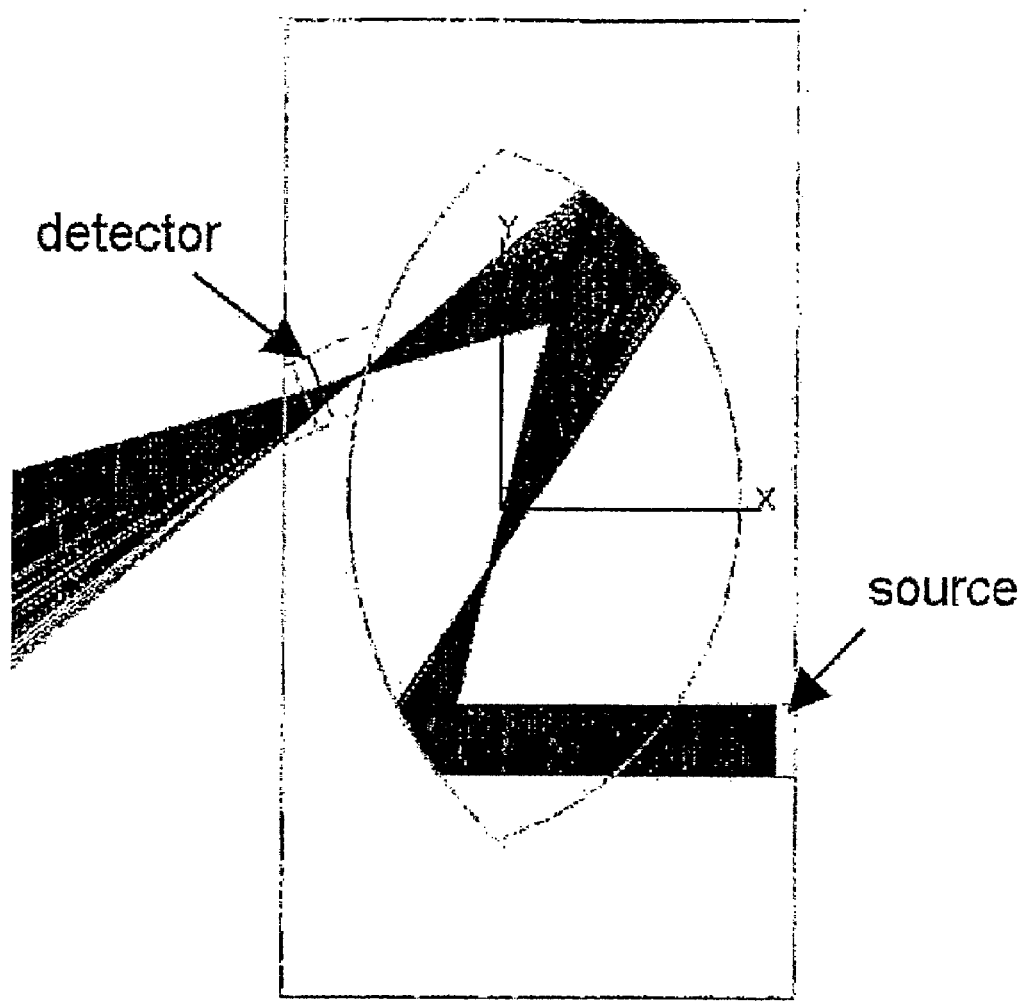
FIG. 17 illustrates the focusing effect of light, which is generated from the optical cavity structure according to the above embodiment.

FIG. 17 illustrates the focusing effect of light, which is generated from the optical cavity structure illustrated in FIG. 15c.

FIG. 17 shows the feature of parallel light irradiated from optical source being intearated to a certain point. In other words, if light is irradiated from the optical source existing at a predetermined position to be parallel to the optical axis on which central points of the circular arcs are located, and reflected twice, it is focused adjacent to the infrared sensor located on the mirror opposite to the optical source, thereby increasing the output voltage of the infrared sensor.

Figure 18:
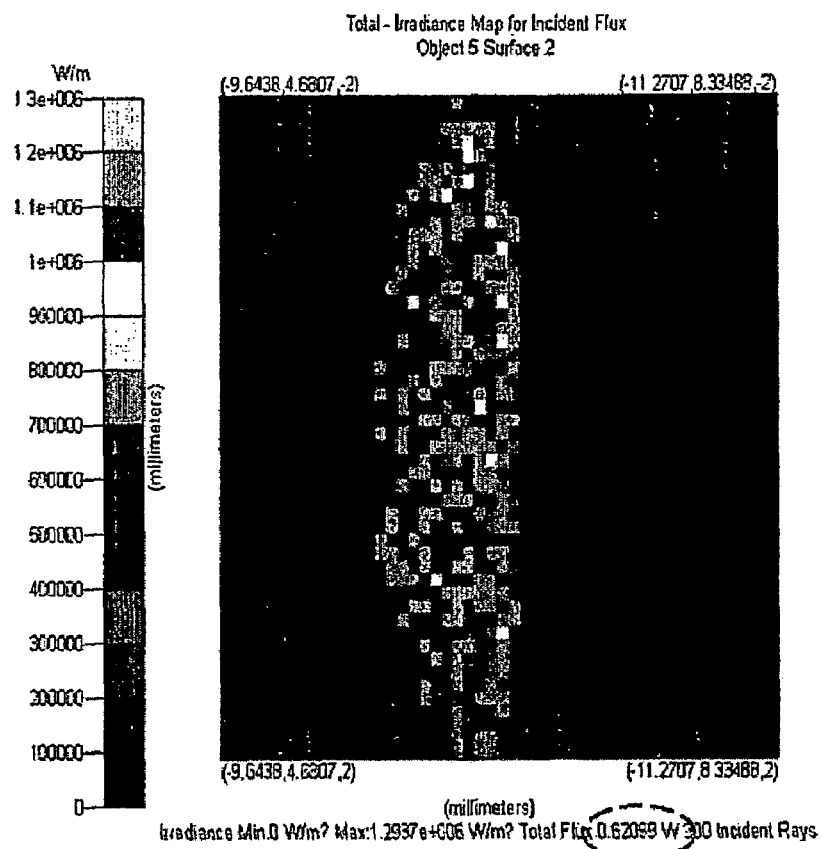
FIG. 18 illustrates a receiving power on a light detector in the optical cavity structure according to the above embodiment of the present invention.

FIG. 18 illustrates a receiving power on a light detector in the optical cavity structure illustrated in FIG. 15c.

In FIG. 18, the location of a light receiving point and the receiving power at each location are colored.

Figure 19A:
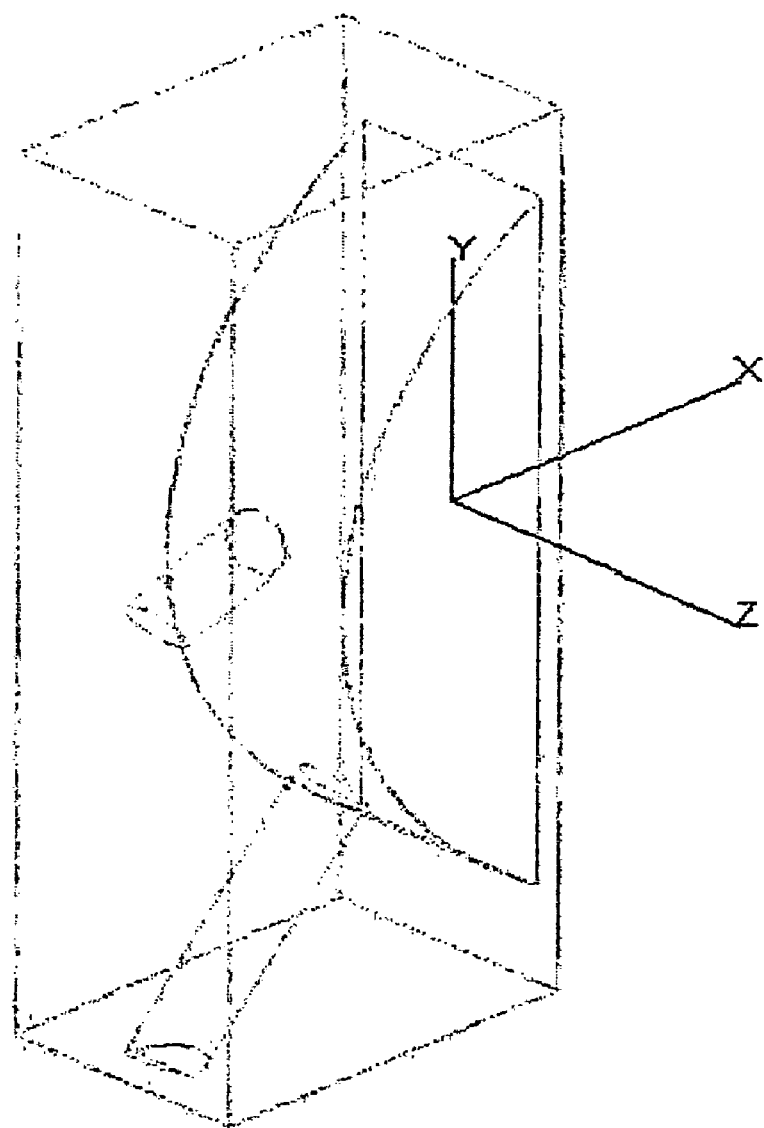
FIG. 19a shows a left half of an optical cavity according to another embodiment of the present invention.
Figure 19B:
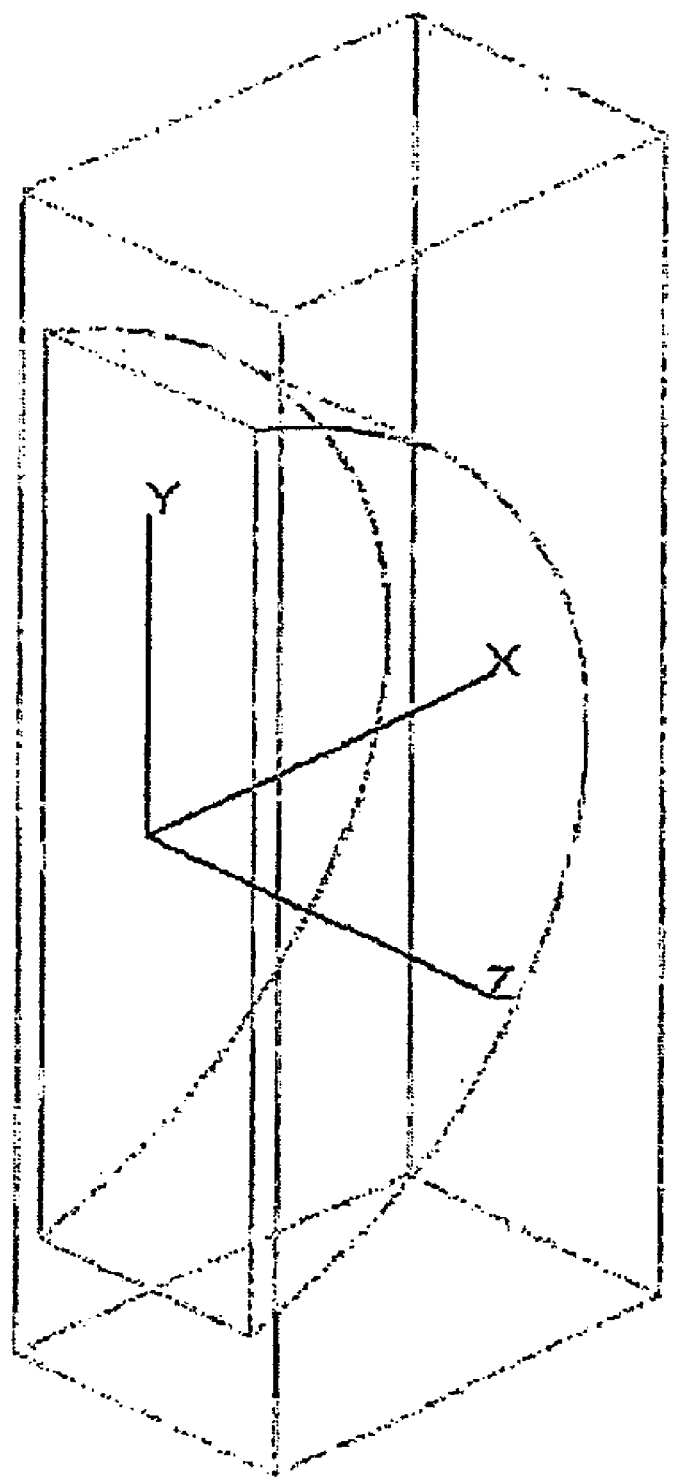
FIG. 19b shows a right half of an optical cavity according to another embodiment of the present invention.

A second simulation has been designed to increase the optical path, which is necessary to detect a small amount of gas. The optical cavity structure illustrated in FIGS. 19a, 19b, and 19c has been applied. The optical cavity of FIG. 19c has combined the left half of FIG. 19a and the right half of FIG. 19b. This combination is only an example, so another optical cavity having different combination still be possible. An integral type of an optical cavity is also possible.

In the second simulation, an optical cavity has been produced using circular arcs which meet the conditions of the optical cavity of the present invention, while applying the structure that if parallel light is irradiated adjacent to the central point (or to the central point) of two circular arcs, the two circular arcs cause the reflected light to reach a certain point near the central axis of the two circular arcs. However, when the number of reflection is increased the light receiving intensity may greatly differ between the simulation and embodiments due to decrease of light intensity in the real embodiments. Thus, on the purport of the simulation, in order to prevent the light receiving intensity from being decreased, the number of reflection has been limited to 5 times until the light reaches an infrared sensor. Also, in the above structure, in order to make light to reach near the center of the circular arcs, a light transmitter (an infrared source) and a light receiver (an infrared sensor) are positioned on the same circular arc. However, the above features are not a restriction of the present invention.

Figure 19C:
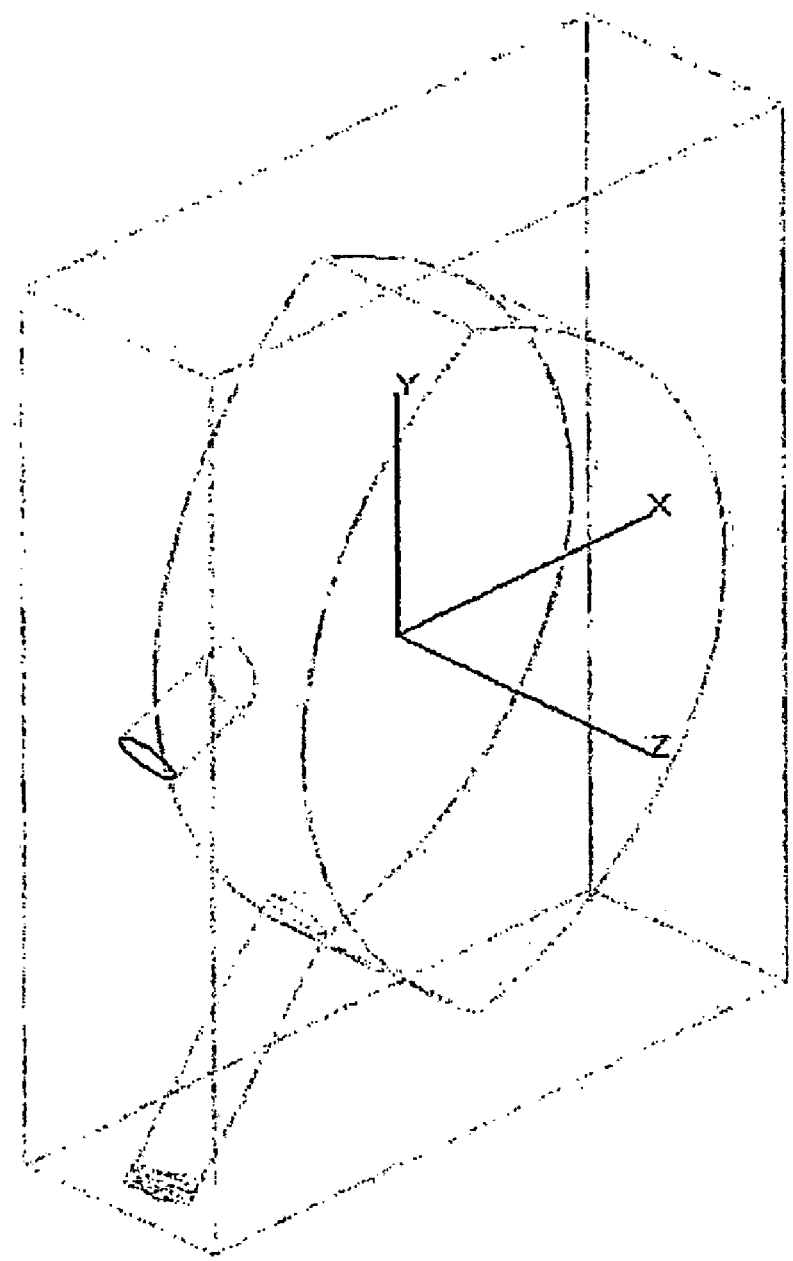
FIG. 19c shows the optical cavity assembled together according to the above embodiment of the present invention.
Figure 20:
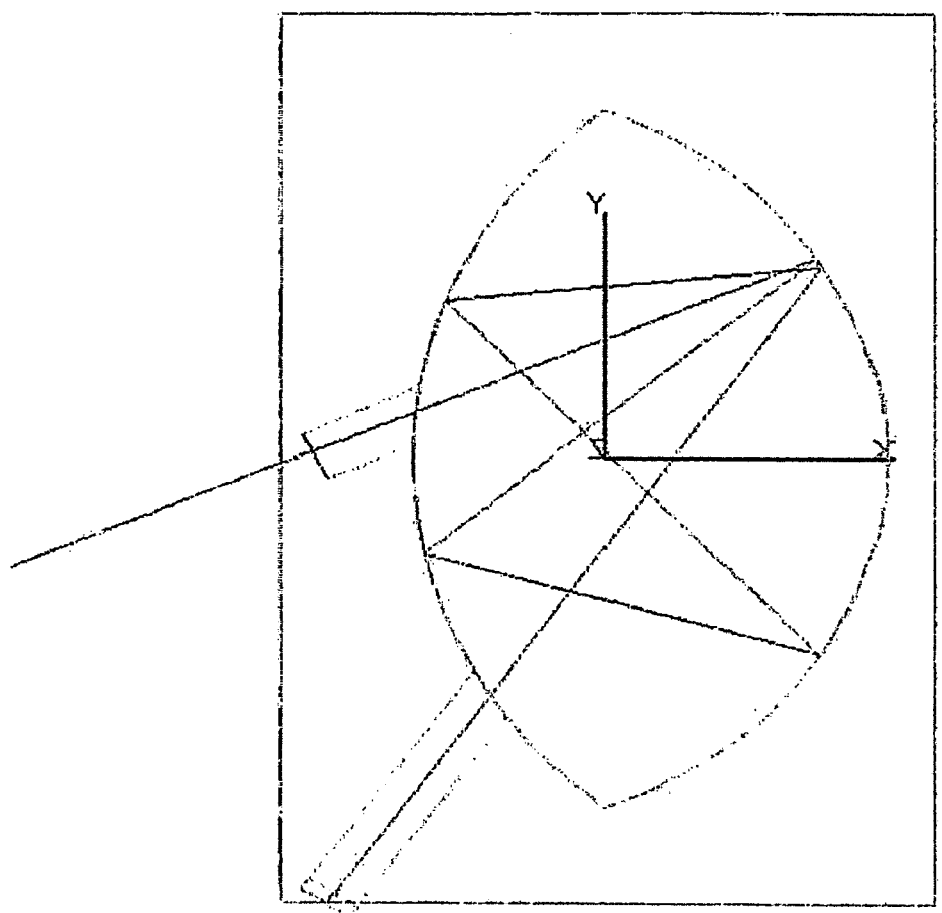
FIG. 20 is an optical path generated from the optical cavity structure according to the above embodiment of the present invention.

FIG. 20 is an optical path generated from the optical cavity structure illustrated in FIG. 19c.

FIG. 20 shows that the light radiated from the light transmitter, particularly the light discharged from the center of the transmitter, reaches the center of the light receiver, i.e., infrared sensor.

Figure 21:
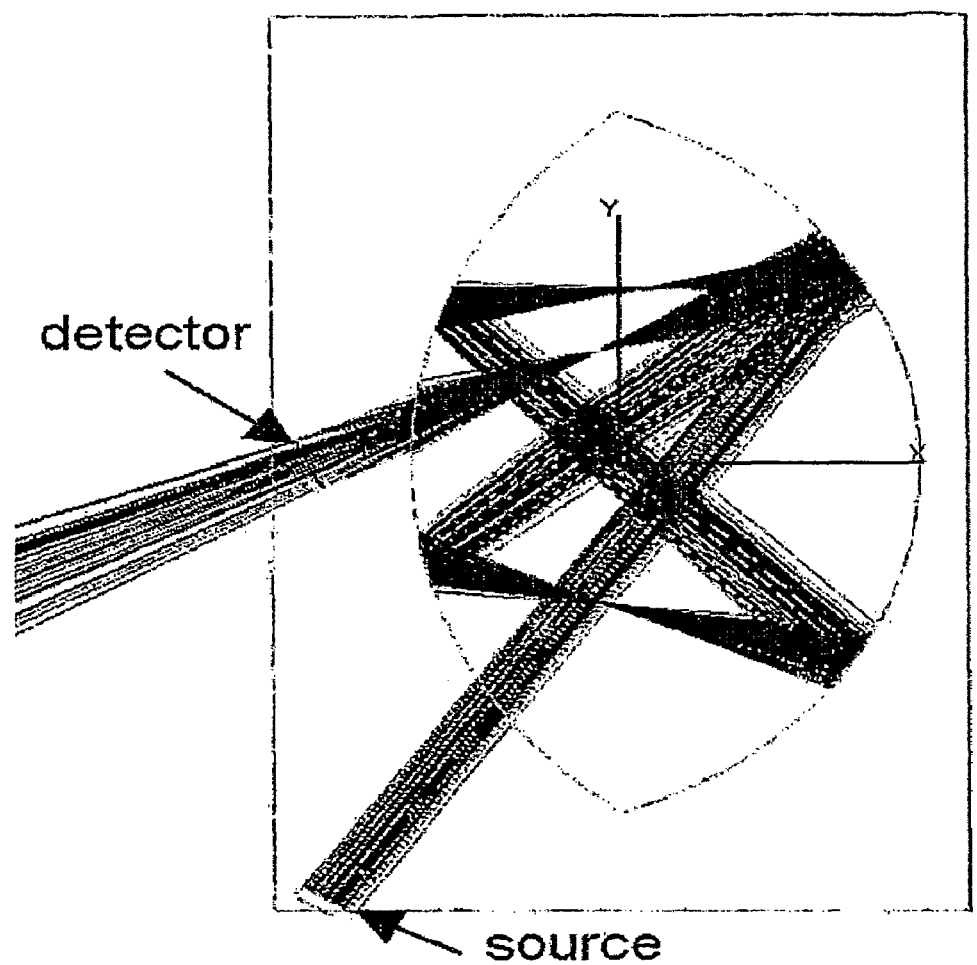
FIG. 21 illustrates the focusing effect of light, which is generated from the optical cavity structure according to the above embodiment of the present invention.

FIG. 21 illustrates the focusing effect of light, which is generated from the optical cavity structure illustrated in FIG. 19c.

FIG. 21 shows that a light bundle being greater than the size (e.g., radius of 2 mm) of the light transmitting part of optical source reaches the light receiver. The optical cavity structure having such configuration can be useful if it is applied to, for example, a multi gas sensor (e.g., sensor radius of 5 mm), which is a light receiver having larger radius than the optical source.

Figure 22:
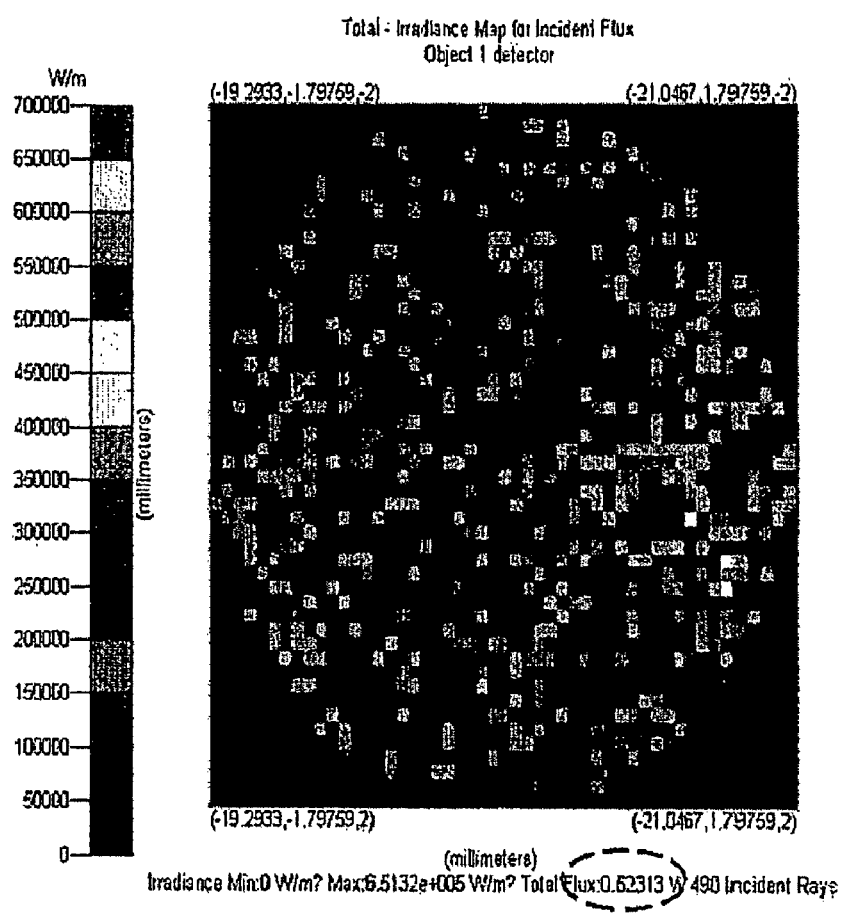
FIG. 22 illustrates a receiving power on a light detector in the optical cavity structure according to another embodiment of the present invention.

FIG. 22 illustrates a receiving power on a light detector in the optical cavity structure illustrated in FIG. 19c.

FIG. 22 shows that the energy of light per unit hour that reaches the light receiving part (round structure) of an infrared sensor is approximately 0.523 watt per hour. Upon comparing it with the ideal energy of 0.567 watt per hour that reaches the infrared sensor without loss after 5 reflections, it is less as much as about 0.44 watt. The reason thereof is assumed because a part of light radiated from the light transmitter is diverged and reaches an area beyond the light receiving part of the infrared sensor.

Upon checking the optical path, focusing effect of light and receiving power of each optical cavity in the above simulations using TracePro®, the following result can be obtained.

The path of light emitted from the central axis of the light transmitter can be confirmed for the entire length of the optical path. The optical cavity according to the present invention can achieve longer optical path than that of the prior art, and the focusing effect of light can be additionally obtained. Also, if the optical source (output voltage: 0.66 watt) works under steady-state condition, it was ascertained that the light intensity reduced by reflectivity of the mirror reaches the light detector. Although the receiving power on the light detector is slightly smaller than the theoretically calculated value, considering that the whole light is not converged into the light detector, it is considered as an appropriate result.

According to the above result of the simulations, particularly, the optical cavity of the first simulation, the following embodiment can be obtained.

The embodiment of the present invention employs two known components, i.e., an infrared optical source and a light detector. For an infrared optical source, for example, the infrared optical source of Gilway technical lamp, which has a parabolic reflector for focusing of parallel light and radiates 1-5 μm infrared, has been used. Also, the ZTP-315 GS thermocouple infrared detector of GE Thermometrics Technologies, which is used for the conventional heating, ventilating and air conditioner (HVAC) application for vehicles, has been employed, but due to the object of gas sensing of this study, the long wavelength band-pass filter has been replaced to the $CO_2$ filter having 4.26 μm central wavelength and 20 nm FWHM (Full Width Half Maximum).

Figure 23:
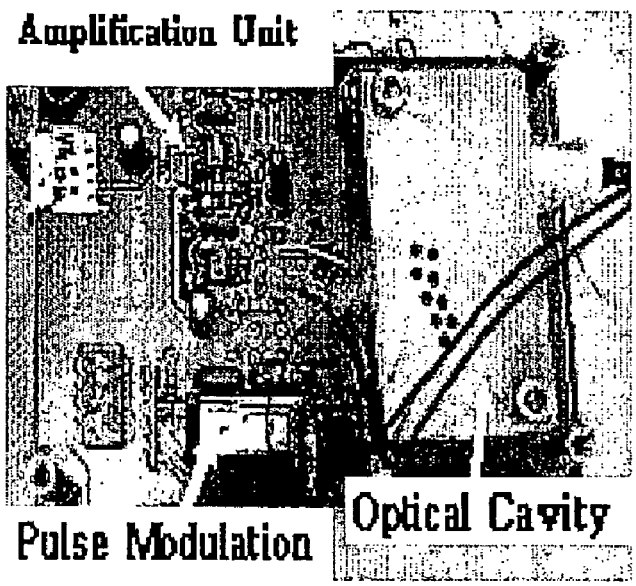
FIG. 23 shows an NDIR gas sensor module according to one embodiment of the present invention.

FIG. 23 illustrates an NDIR gas sensor module according to the above embodiment of the present invention, which consists of three main parts. The first part is an infrared modulating part wherein pulse duration time is 200-600 ms, and turn-off time is changed from 2 sec. to 3 sec. with 0.5 sec. interval. The second part is a new optical cavity structure suggested by the present invention. The third part is an amplifying circuit. In the embodiment, a secondary amplifying circuit having a reference voltage driver (LM 385) has been used.

Figure 24:
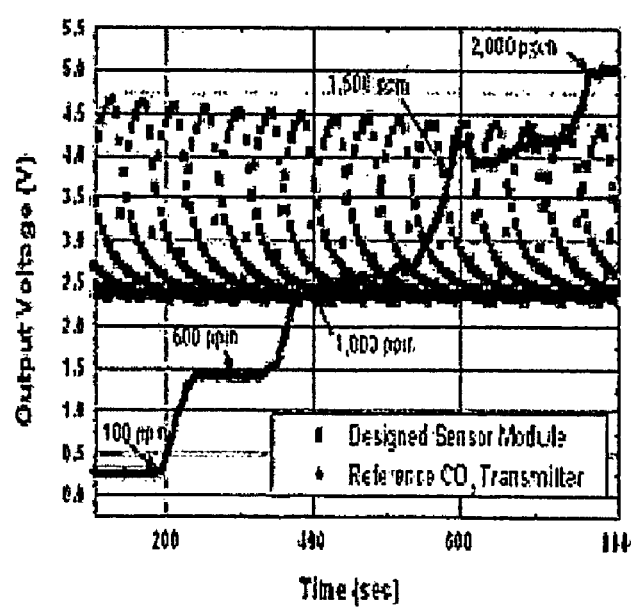
FIG. 24 illustrates a feature of an output voltage according to $CO_2$ gas concentration at a room temperature to the NDIR gas module according to the above embodiment of the present invention.

FIG. 24 illustrates an output voltage versus $CO_2$ gas concentration at a room temperature for an NDIR gas module and a reference transmitter according to the above embodiment of the present invention. As shown in FIG. 24, the maximum output voltage of the new sensor module is about 4.75V at $CO_2$ gas concentration of 100 ppm. As the $CO_2$ gas concentration increases between 100-2,000 ppm, the maximum peak voltage of the sensor module is reduced to 4.45V. The maximum difference of the peak voltage under the above $CO_2$ gas concentration variation between 100-2,000 ppm is 300 mV.

Figure 25:
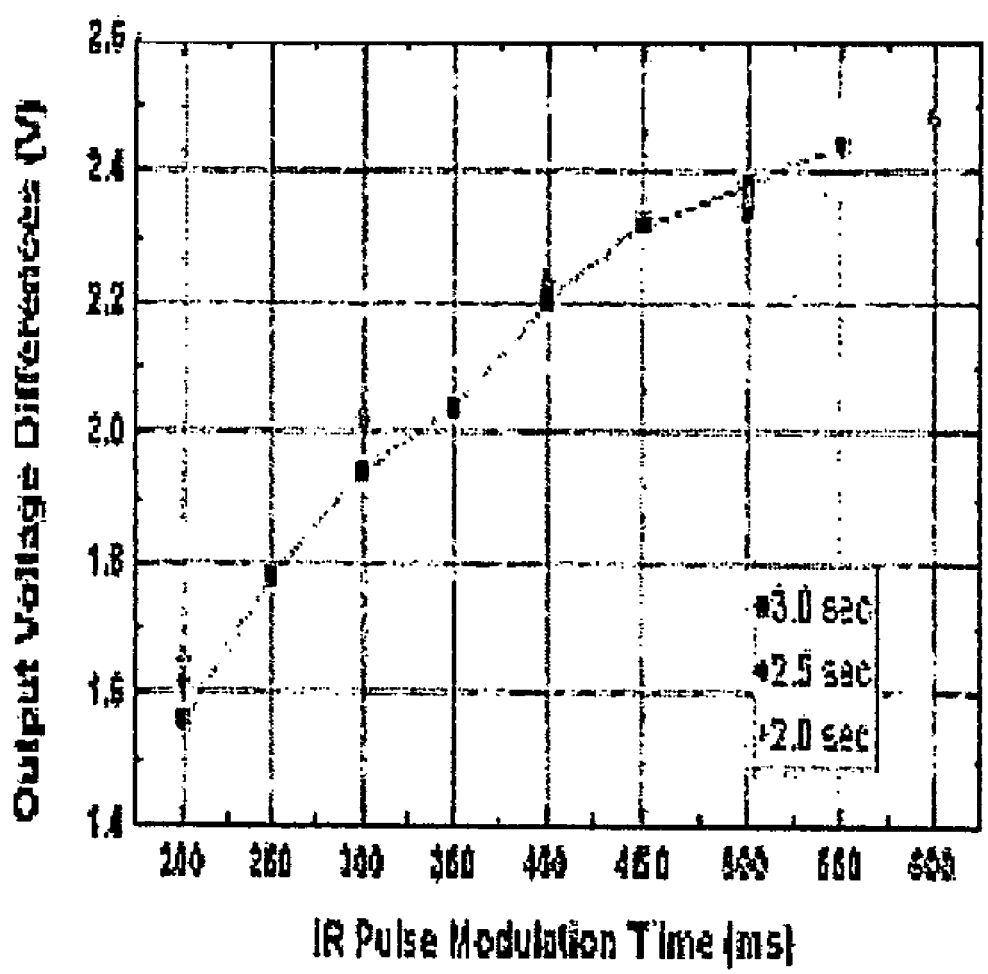
FIG. 25 illustrates changes of the output voltage according to the pulse modulation time of the NDIR gas sensor module according to the above embodiment of the present invention.

FIG. 25 illustrates the output voltage difference according to the pulse modulation time when $CO_2$ gas concentration is consistent in the above embodiment of the present invention. The output voltage difference means the difference between the output voltage in the turn-on state of the optical source and the output voltage in the turn-off state of the optical source. As the pulse modulation time increases, the output voltage difference also increases. However, if the pulse modulation time exceeds, 500 ms, the output voltage difference begins to be saturated. Accordingly, the output voltage also becomes to have little difference between each other. Also, since the absorbed infrared intensity is high, discharge of the absorbed heat is not conducted completely and the lifetime of the optical source becomes shortened.

Figure 26:
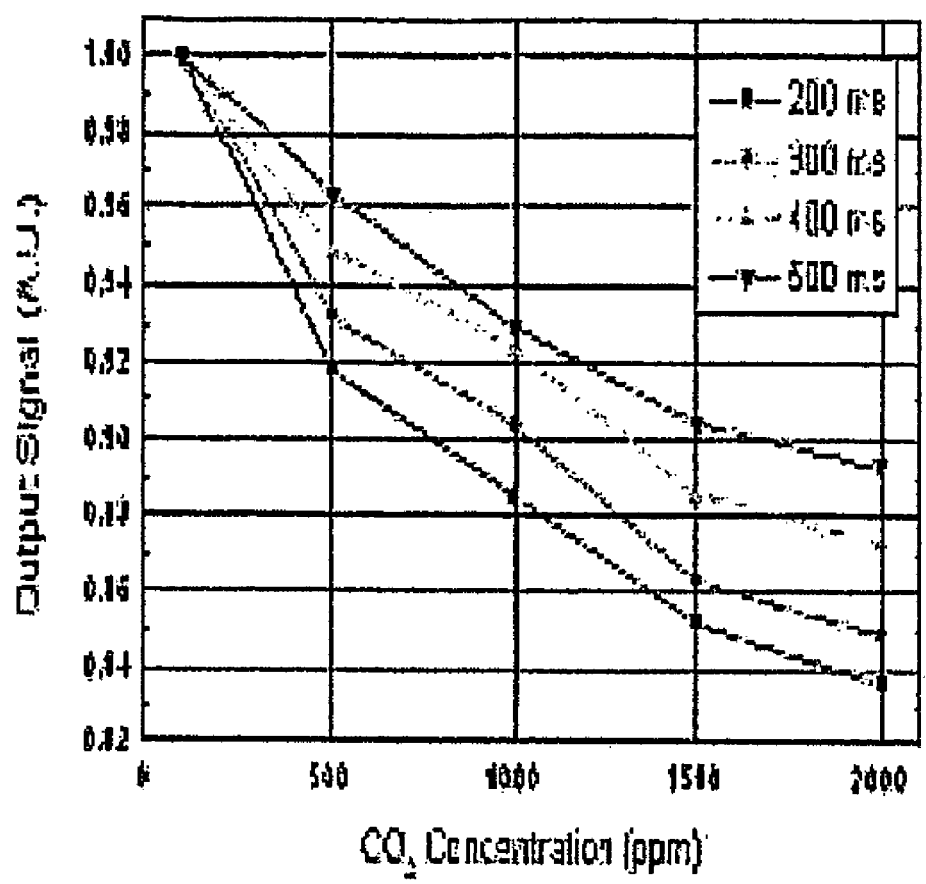
FIG. 26 illustrates changes of the output voltage according to $CO_2$ gas concentration to the NDIR gas sensor module according to the above embodiment of the present invention.

FIG. 26 illustrates changes of the output voltage according to the change of $CO_2$ gas concentration in the above embodiment of the present invention. It shows normalized output signals of the NDIR sensor module when the $CO_2$ gas concentration increases between 100-2,000 ppm. The normal output signal exhibits the maximum change when the infrared pulse modulation time is 200 ms. As the modulation time increases between 300-500 ms, the normal output signal is considerably reduced.

Meanwhile, the maximum voltage difference is shown at 500 ms of pulse duration time, but simultaneously the reference voltage slightly increases. The change of the output voltage becomes maximum at 200 ms of pulse duration time, and exhibits 18,000 times of amplification gain. At this time, the turn-off time of the infrared optical source is 3 sec.

Although the present invention has been described with reference to particular embodiments of the NDIR gas sensor and the optical cavity, the description is only an example of the invention's application and should not be taken as limiting the scope of the present invention. Various adaptations and combinations of simulations and the embodiments disclosed are within the scope of the invention as defined by the appended claims.

For example, in order to obtain the parallel light of the present invention, another method of producing a parabolic type mirror in an optical cavity can be employed for production of a cost-effective optical cavity, and the present invention can be implemented using laser source having a predetermined wavelenath without the use of the IR lamp from Gilway™.

INDUSTRIAL APPLICABILITY

As described above, according to the optical gas sensor according to the present invention, the length of the optical path, which has been projected from the infrared optical source, becomes considerably increased, and it is possible to measure gases from low concentration to high concentration. Also, various kinds of gases can be measured.

In addition, two concave mirrors have been used for the gas chamber wall, thereby achieving the effects of easy design and production of a gas sensor and reducing manufacturing cost.

The present invention has proposed a new gas sensor structure by improving the design of the optical cavity for the conventional NDIR gas sensor. The optical cavity structure of the present invention is very simple, which consists of two concave mirror surfaces, and the light bundle is focused on the light detector.

According to the present invention, a new optical cavity structure for an NDIR gas sensor having extended optical path and focusing feature of light can be obtained. By using the new optical cavity structure, a new sensor module can be obtained for air quality measuring system, HVAC system for vehicles, etc.

The invention claimed is:

1. An optical gas sensor comprising a gas chamber for housing a sample gas; a gas opening for injecting the sample gas into the gas chamber or for exhausting the sample gas from the gas chamber; an infrared optical source for projecting infrared toward the sample gas; and an infrared sensor for sensing the intensity of the infrared which has passed through the sample gas, characterized in that:

the wall of the gas chamber is composed of two opposing concave mirrors having different focusing distances but a common focus, and the concave mirrors have curvatures such that the incident light which is parallel to the axis of the concave mirror reflects on the surface of the concave mirror and passes through the common focus of the concave mirror, and that the incident light, which has passed through the common focus of the concave mirror reflects on the surface of the concave mirror and propagates parallel to the axis of the concave mirror.

2. The optical gas sensor according to claim 1, wherein the gas opening comprise a gas vent located at a certain wall of the gas chamber and a plurality of gas diffusion holes disposed on the lower or upper support plate of the gas chamber.

3. The optical gas sensor according to claim 2, wherein the plurality of gas diffusion holes is covered by a gas filter.

4. The optical gas sensor according to claim 3, wherein the plurality of gas diffusion holes are preferably disposed on the axis of the incident light from the infrared sensor.

5. The optical gas sensor according to claim 2, wherein the gas vent is curved downward or equipped with a detachable cap.

6. The optical gas sensor according to claim 1, wherein the surface of the concave mirror is plated by or deposited with gold.

7. The optical gas sensor according to claim 2, wherein the gas chamber contains a parabolic reflecting mirror integrally formed with the support plate of the gas chamber adjacent to the infrared optical source formed at the support plate.

8. The optical gas sensor according to claim 7, wherein a light outlet for projecting at least a part of the infrared light from the infrared optical source is formed on the support plate of the gas chamber.

9. The optical gas sensor according to claim 7 or 8, wherein the infrared optical source is disposed on the focus of the parabolic mirror.

10. The optical gas sensor according to claim 2, wherein the lower support plate of the gas chamber is attached with a height compensation structure for compensating the inclination of the support plate due to the height of the infrared optical source.

11. An optical gas sensor comprising a gas chamber for housing a sample gas; a gas opening for injecting the sample gas into the gas chamber or for exhausting the sample gas from the gas chamber; an infrared optical source for projecting infrared toward the sample gas; and an infrared sensor for sensing the intensity of the infrared which has passed through the sample gas, characterized in that:

the wall of the gas chamber is composed of two opposing concave mirrors having different focusing distances but a common focus.

12. The optical gas sensor according to claim 11, wherein the gas opening comprise a gas vent located at a certain wall of the gas chamber and a plurality of gas diffusion holes disposed on the lower or upper support plate of the gas chamber.

13. The optical gas sensor according to claim 12, wherein the plurality of gas diffusion holes are covered by gas filters.

14. The optical gas sensor according to claim 11, wherein the surface of the concave mirror is plated by or deposited with gold.

15. The optical gas sensor according to claim 12, wherein the gas chamber contains a parabolic reflecting mirror formed so that the parabolic reflecting mirror causes the incident light from the infrared optical source to propagate in parallel with the lower or upper support plate of the gas chamber.

16. An optical cavity for a non-dispersive infrared sensor, characterized in that:

the optical cavity is formed by two opposing concave mirrors, the cross-section of the concave mirror is a circular arc, the central points of the two circular arcs exist on the same axis, and the optical cavity is optically closed except for holes for optical source, optical detector, gas vent and gas diffusion.

17. The optical cavity according to claim 16, wherein the central point of each circular arc coincides with the middle point of the straight line going from one circular arc to the other circular arc.

18. The optical cavity according to claim 16 or 17, wherein the circular arcs have different radius from each other.

19. The optical cavity according to claim 18, wherein the central point of the circular arc having a longer radius exists outside of the circular arc having a shorter radius, and the central point of the circular arc having a shorter radius exists inside of the circular arc having a longer radius.

20. The optical cavity according to claim 19, wherein the optical source and the optical detector are located on a different circular arc, and an incident light from the optical source is irradiated in parallel with the axis on which the central points of the two circular arcs are located, reflected once on each of the circular arc and detected by the optical detector.

21. The optical cavity according to claim 20, wherein the parallel light irradiated from the optical source focuses on the circular arc where the optical detector is located.

22. The optical cavity according to claim 17, wherein the optical source and the optical detector are located on the same circular arc, and an incident light from the optical source is reflected odd number of times on each of the circular arc and detected by the optical detector.

23. The optical cavity according to claim 22, wherein the incident light from the optical source incidents to or adjacent to a center of the optical cavity, repeats convergence and divergence during the plurality of reflections and reaches the optical detector, and wherein the cross-sectional area of the light reaching the circular arc on which the optical detector is located is larger than that of the light irradiated from the optical source.

24. An optical cavity for a non-dispersive infrared sensor comprising:

an optical source for irradiating infrared light;

an optical detector for ultimately detecting the infrared light from the optical source;

an optical cavity formed by two opposing concave mirrors, wherein the cross-section of the concave mirror is a circular arc, the central points of the two circular arcs exist on the same axis, and the optical cavity is optically closed except for holes for optical source, optical detector, gas vent and gas diffusion;

an optical modulating means for controlling the infrared light irradiated from the optical source, wherein the optical modulating means has a pulse modulation time of 200-600 ms and turn-off time of 2 sec., 2.5 sec. and 3 sec.; and an amplification means for amplifying an electrical signal from the optical detector.

25. The optical cavity according to claim 24, wherein the optical modulating means sets the optical source with a pulse modulation time of 200 ms and turn-off time of 3 sec.

* * * * *